(12) United States Patent
Nishiyama et al.

(10) Patent No.: US 7,625,747 B2
(45) Date of Patent: Dec. 1, 2009

(54) FEED CONTROLLING APPARATUS

(75) Inventors: Shusaku Nishiyama, Kawasaki (JP); Sachihiro Youoku, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 508 days.

(21) Appl. No.: 11/008,961

(22) Filed: Dec. 13, 2004

(65) Prior Publication Data

US 2006/0040374 A1  Feb. 23, 2006

(30) Foreign Application Priority Data

Aug. 20, 2004  (JP) ............................ 2004-240329

(51) Int. Cl.
   *C12M 1/00* (2006.01)
   *C12M 3/00* (2006.01)
(52) U.S. Cl. .................................................. 435/285.1
(58) Field of Classification Search ............... 435/285.1
   See application file for complete search history.

(56) References Cited

U.S. PATENT DOCUMENTS

| | | | | |
|---|---|---|---|---|
| 2,844,350 A | * | 7/1958 | Higham et al. ............... | 177/122 |
| 3,498,395 A | * | 3/1970 | Henry ........................... | 177/1 |
| 6,531,285 B1 | * | 3/2003 | Chen ............................. | 435/6 |
| 6,645,757 B1 | * | 11/2003 | Okandan et al. ........... | 435/285.1 |
| 6,695,165 B2 | * | 2/2004 | Park ............................. | 220/812 |

FOREIGN PATENT DOCUMENTS

| | | |
|---|---|---|
| JP | 5-18887 | 1/1993 |
| JP | 6-225750 | 8/1994 |
| WO | WO00/20554 | * 4/2000 |

* cited by examiner

*Primary Examiner*—Walter D Griffin
*Assistant Examiner*—Lydia Edwards
(74) *Attorney, Agent, or Firm*—Arent Fox LLP

(57) ABSTRACT

A feed controlling apparatus that controls feeding of plural minute objects that flow along a channel of a fluid, and receive a predetermined process at a predetermined position, includes a detector that detects whether there is the object at the predetermined position, and a controller that controls feeding of the object to be supplied to the predetermined position based on a detection result by the detector.

6 Claims, 13 Drawing Sheets

US 7,625,747 B2

FEED CONTROLLING APPARATUS

This application claims the right of foreign priority under 35 U.S.C. §119 based on Japanese Patent Application No. 2004-240329, filed on Aug. 20, 2004, which is hereby incorporated by reference herein in its entirety as if fully set forth herein.

BACKGROUND OF THE INVENTION

The present invention relates generally to feed controls over minute floating objects that spread in the fluid. The present invention is suitable, for example, for a feed controlling apparatus and method that feed minute floating cells in a drug discovery system that investigates reactions of biogenetic cells, such as leukocytes' antibody generations, for use with a medical field. The "drug discovery system", as used herein, generally means a system that processes a cell, e.g., injects extrinsic gene and medication solutions using a fine needle or a capillary into a cell, then cultivates each processed cell, independently evaluate or process the cell (e.g., by screening and antibody extraction).

Recently, opportunities of using cells, to which gene and medication are injected, have increased in the field of regenerative medicine and genome-based drug discovery, etc. Unlike the research application, it is necessary in this medical application to previously determine a combination between a cell and an introduced material and to independently evaluate each cell, e.g., observe whether or not there is an effect expression in a single cell. In addition, the medical application requires a predetermined throughput to be maintained in processing a large amount of cells.

A transgenetic method includes a biological approach, such as a vector method, a chemical approach, such as a transfection, and a physical approach, such as an electroporation, a particle gun and an injection. The biological and chemical approaches are not suitable for the medical application because they limit combinations between cells and introduced materials. On the other hand, the physical approach is known as a method that does not limit the combinations. In particular, the injection approach (see, for example, Japanese Patent Applications, Publication Nos. 5-192171, 6-343478 and 2000-23657) has a high introduction success rate as widely used for artificial inseminations, and is likely to be adopted as a next-generation transgenetic method. According to the prior art injection approach, a skilled operator uses a microscope to introduce a material from a needle tip into a cell while minimizing damages to the cell.

Other prior art include, for example, Japanese Patent Applications, Publication Nos. 6-225750 and 5-18887.

However, the conventional injection approach has a problem of a low throughput, since it needs manual operations to a laboratory dish under the microscope field, and manual feeding to an incubator after the gene is injected. Therefore, the conventional injection approach is suitable for an environment that handles the small number of necessary cells as in the artificial insemination, but unsuitable for industrial applications, such as the regenerative medicine and genome-based drug discovery. In addition, the conventional injection approach handles cells that are irregularly arranged in a laboratory dish or a group of introduced cells, and has difficulties in independently evaluating each cell as required by the medical application.

BRIEF SUMMARY OF THE INVENTION

Accordingly, it is an exemplary object to provide a feed controlling apparatus and method, which improve the throughput and provide independent evaluations while adopting the injection approach that has no restriction to a combination of a cell and an introduced material, and has a high success rate.

A feed controlling apparatus according to one aspect of the present invention that controls feeding of plural minute objects that flow along a channel of a fluid, and receive a predetermined process at a predetermined position, includes a detector that detects whether there is the object at the predetermined position, and a controller that controls feeding of the object to be supplied to the predetermined position based on a detection result by the detector. Since this feed controlling apparatus can stop supplying the object when another object is located at the predetermined position, this feed controlling apparatus can solve the problems of simultaneous supplies of plural objects to the predetermined position, a collision of one object with another object that is being processed, causing a prevention of the process or a flow of the other object before its process completes (i.e., flowing of an outstanding object downward).

A feed controlling apparatus according to another aspect of the present invention that controls feeding of plural minute objects that have received a predetermined process at a predetermined position and flow along a channel of a fluid, includes a detector that detects a result of the predetermined process, and a controller that determines, based on a detection result by the detector, a feed path through which a processed object is to flow from the predetermined position. Since this feed controlling apparatus can sort a feed path based on a success or a failure of the process, it is possible to flow unsuccessfully processed objects to a feed path for disposal and to flow only successfully processed objects to a feed path for recovery. Since only the successfully processed objects are recovered, the subsequent analysis and evaluation processions improve.

A feed controlling apparatus according to still another aspect of the present invention that controls feeding of plural minute objects, and receive a predetermined process at a predetermined position, includes a channel that feeds the objects one by one to the predetermined position, a gate member that varies between a first state that allows the object to be fed along the channel, and a second state that prevents the object from being fed along the channel, and a controller that controls the gate member so that the controller varies the gate member to the first state when determining that there is no object at the predetermined position, and the gate member to the second state when determining that there is the object at the predetermined position. This feed controlling apparatus can restrict flow directions of the objects using the channel, and stop supplying the object when there is another object at the predetermined position by using the gate member. Therefore, this feed controlling apparatus can solve the problems of simultaneous supplies of plural objects to the predetermined position, a collision of one object with another object that is being processed, causing a prevention of the process or a flow of the other object before its process completes (i.e., flowing of an outstanding object downward).

Preferably, the gate member puts the objects on standby one by one in order along the channel, thereby forming a waiting line of the objects. A production of a continuous waiting line of the objects enables the objects to be processed continuously at regular time intervals. In other words, if the object's concentration in the channel is not constant, the object might become slow to reach the predetermined position or plural objects might reach the injecting position at the same time. This case would make irregular a time interval of the process and lower the throughput. However, if plural objects are put on standby, the object is processed while the waiting line is being formed, for example, and the process efficiency improves.

Preferably, the gate member at the second state blocks the object while allowing the fluid to pass the gate member. Thereby, the object always receives a downstream force, and the gate member can serve as means for capturing the object at the predetermined position. This structure prevents the overflow of the fluid from the channel.

The gate member includes, for example, at least a pair of gates arranged at an upstream side to the predetermined position along the channel. The gate has, for example, a pile or door shape. The feed controlling apparatus may further include a piezoelectric element that serves as a drive unit that turns the gate member between the first and second states. The piezoelectric element is highly responsive, and suitable for the drive unit. The controller may turn the gate member to the first state, when determining that the processed object moves downstream by a predetermined distance from the predetermined position, so as to prevent a collision of the objects at the predetermined position.

A feed controlling apparatus that controls feeding of plural minute objects that have received a predetermined process at a predetermined position, includes a channel, connected to a recovery part and a disposal part, which feeds the objects one by one from the predetermined position, a gate member that varies between a first state that allows the object to be fed to the recovery part along the channel, and a second state that allows the object to be fed to the disposal part along the channel, and a controller that controls the gate member so that the controller varies the gate member to the first state when determining that the process has succeeded, and the gate member to the second state when determining that the process has failed. This feed controlling apparatus can restrict flow directions of the objects using the channel, and sort a feed path based on a success or a failure of the process using the gate member. It is possible to flow unsuccessfully processed objects to a feed path for disposal and only successfully processed objects to a feed path for recovery. Since only the successfully processed objects are recovered, the subsequent analysis and evaluation processions improve.

The controller may determine, based on a size of the object, whether the process (such as an injection process) has succeeded or failed. The feed controlling apparatus may further include a first counter that counts the number of successes of the process by detecting that the gate member has varied to the first state, and a second counter that counts the number of failures of the process by detecting that the gate member has varied to the second state, wherein the controller calculates at least one of a success rate of the process and a continuous failure number of the process based on detection results of the first and second counters. Thereby, the feed controlling apparatus can immediately and automatically detect and inform an operator of the abnormality of the processing unit.

The gate member may be provided on the channel to the recovery part, and the feed controlling apparatus may further include a storage that stores and supplies a predetermined amount of objects to the recovery part. Thereby, a predetermined amount of objects necessary for the recovery part can be easily supplied to the recovery part. The feed controlling apparatus preferably includes a detector (such as an image processor) that detects whether a predetermined amount of objects are stored in the storage, so as to store the predetermined amount without fail.

The object is, for example, a cell, and the predetermined process is, for example, an injection of gene and medication solutions to the cell by using a capillary.

A feed controlling apparatus according to another aspect of the present invention that controls feeding of plural cells to a recovery part from a predetermined position at which a predetermined material is injected into each cell in a cell suspension by using a capillary, includes a storage that stores injected cells, and a controller that simultaneously supplies a predetermined amount of injected cells to the recovery part when determining that the predetermined amount of injected cells are stored in the storage. Since a cell needs a certain concentration for incubation and division, this feed controlling apparatus easily and definitely provides the recovery part with a predetermined amount of cells necessary for the recovery part.

A feed controlling method according to still another aspect of the present invention that utilizes two or more gates located at an upstream side to a predetermined position along a channel of a fluid, and controls feeding of plural minute objects that flow the channel and receives a predetermined process at the predetermined position by a processing unit, includes a first step of determining whether the object comes down stream close to the predetermined position, a second step of opening a first gate that is located upstream among the gates, and of allowing the object to pass the first gate, a third step of determining whether the object is filled in a space between the gates, a fourth step of closing the first gate and of blocking a flow of the objects, when the third step determines that the object is filled in the space, a fifth step of determining whether the predetermined process by the processing unit is available, and a sixth step of opening a second gate that is located downstream among the gates, and of allowing the object to pass the second gate, when the fifth step determines that the predetermined process is available. This feed controlling apparatus can stop supplying the object when there is another object at the predetermined position by using the gate member. Therefore, this feed controlling apparatus can solve the problems of simultaneous supplies of plural objects to the predetermined position, a collision of one object with another object that is being processed, causing a prevention of the process or a flow of the other object before its process completes (i.e., flowing of an outstanding object downward).

A feed controlling method according to another aspect of the present invention that utilizes two or more gates located at an upstream side to a predetermined position along a channel of a fluid, and controls feeding of plural minute objects that flow the channel and receives a predetermined process at the predetermined position by a processing unit, includes a first step of closing the most downstream gate and of opening gates other than the most downstream gate, a second step of sequentially closing the gates opened by the first step so that each space between two adjacent gates is sequentially filled with the object in order from a downstream side, a third step of determining whether each of all the spaces among the gates is filled with the object, a fourth step of determining whether the predetermined process by the processing unit is available when the third step determines that each of all the spaces among the gates is filled with the object, and a fifth step of sequentially opening the gates in order from a downstream side and of allowing the objects to pass the gates that have been opened, when the fourth step determines that the predetermined process is available. This feed controlling apparatus stops supplying the object when there is another object at the predetermined position by using the gate. Therefore, this feed controlling apparatus can solve the problems of simultaneous supplies of plural objects to the predetermined position, a collision of one object with another object that is being processed, causing a prevention of the process or a flow of the other object before its process completes (i.e., flowing of an outstanding object downward). In addition, the gate can form a waiting line of the object. A production of a continuous waiting line of the objects enables the objects to be processed continuously at regular time intervals. In other words, if the object's concentration in the channel is not constant, the object might become slow to reach the predetermined position or plural objects might reach the injecting position at the same time. This case would make irregular a time interval for the process and lower the throughput. However, if plural objects are put on standby, the object is processed while the waiting line is being formed, for example, and the process efficiency improves.

The feed controlling method may further include a sixth step of resuming with the first step after the objects among all the gates are supplied to the predetermined position. Alternatively, the feed controlling method may further include a sixth step of supplementing a new object between a pair of the most upstream gates whenever the object between a pair of downstream gates moves downstream.

A feed controlling method according to still another aspect of the present invention that utilizes two or more gates located at an upstream side to a predetermined position along a channel of a fluid, and controls feeding of plural minute objects that flow the channel and have received a predetermined process at the predetermined position by a processing unit, includes a first step of determining whether the predetermined process has succeeded or failed, a second step of opening one of the gates and of allowing the object to flow along a first feed path to a recovery part when the first step determines that the predetermined process has succeeded, and a third step of opening another of the gates and of allowing the object to flow along a second feed path to a disposal part when the first step determines that the predetermined process has failed. Thereby, only the successfully processed objects can be supplied to the recovery part without fail.

The feed controlling method may further include a fourth step of closing a gate that prevents a backflow of the object after the object flows to the first feed path as a result of the second step. Thereby, an amount of objects necessary for the recovery part can be supplied to the recovery part without fail. The feed controlling method may further include a fourth step of determining whether a predetermined amount of objects are stored in the first feed path, and a fifth step of opening a gate that stores the cell when the fourth step determines that the predetermined amount of objects are stored. Thereby, an amount of objects necessary for the recovery part can be supplied to the recovery part without fail. The feed controlling method may further include a fourth step of determining whether at least one of the success rate of the process or the continuous failure number is below a predetermined threshold, and a fifth step of waning the abnormality of a processing unit that provides the predetermined process. This structure can inform an operator of the abnormality of the processing unit easily and immediately.

A processing system according to another aspect of the present invention includes an injector that automatically injects a predetermined material into plural minute objects that flow along a channel of a fluid, at a predetermined position by using a capillary, and a feed controlling apparatus that automatically controls feeding of the objects to the predetermined position based on whether the object is located at the predetermined position. This processing system improves the success rate of the injection using the injection approach, and stop supplying the objects when there is the object at the predetermined position using the feed controlling apparatus. Thereby, this processing system can solve the problems of simultaneous supplies of plural objects to the predetermined position, a collision of one object with another object that is being processed, causing a prevention of the process or a flow of the other object before its process completes (i.e., flowing of an outstanding object downward).

A processing system according to another aspect of the present invention includes an injector that automatically injects a predetermined material into plural minute objects that flow along a channel of a fluid, at a predetermined position by using a capillary, and a feed controlling apparatus that determines a feed path for an injected object based on whether an injection by the injector has succeeded or failed. This processing system improves the success rate of the injection using the injection approach, and the feed controlling apparatus sorts a feed path based on a success or a failure of the process. Therefore, it is possible to flow unsuccessfully processed objects to a feed path for disposal and only successfully processed objects to a feed path for recovery. Since only the successfully processed objects are recovered, the subsequent analysis and evaluation processions improve.

Other objects and further features of the present invention will become readily apparent from the following description of the preferred embodiments with reference to accompanying drawings.

DETAILED DESCRIPTION OF THE PREFERRED EMBODIMENTS

Figure 1:
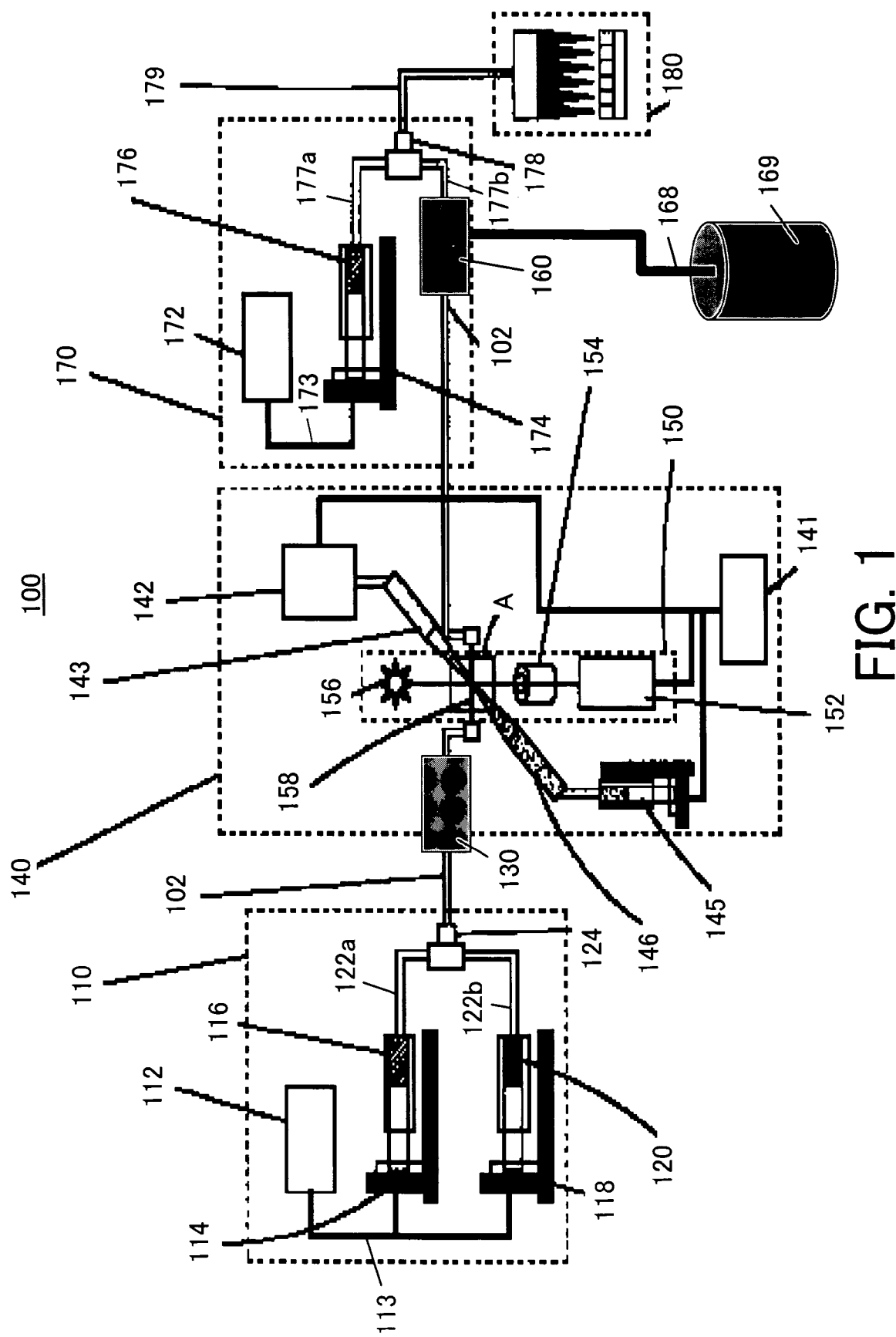
FIG. 1 is a schematic block diagram of a cell processing system according to one aspect of the present invention.

A description will now be given of a cell processing system 100 according to one embodiment of the present invention, with reference to the accompanying drawings. The cell processing system 100 is one example of an inventive processing system, and provides a predetermined process (for example, an injection process) to minute objects applicable to the present invention. The minute objects can float on the fluid, such as the cell suspension and medium, and are fed along the fluid's channel that restricts the flowing direction. Here, FIG. 1 is a schematic block diagram of a cell processing system 100. The cell processing system 100 includes, as shown in FIG. 1, a first feeding unit 110, a feed controlling apparatus 130, an injector 140, a feed controlling apparatus 160, a second feeding unit 170, a collection container 169 and a dispenser unit 180. The cell processing system 100 uses the channel (or pipelines 102 and 179) and the first and second feeding units 110 and 170, feeds the cells in the cell suspension along the channel, and provides a large amount of cells with the injection process while maintaining the predetermined throughput.

The first feeding unit 110 is located an upstream side of the injector 140 via a pipeline 102, and feeds the cell suspension. The first feeding unit 110 includes a controller 112, feeders 114 and 118, and a mixer 124. The feeder 114 sends out a medium 116, and the feeder 118 sends out the cell suspension 120. The controller 112 is connected to the feeders 114 and 118 via a wiring 113, and controls their sending actions. The feeder 114 is connected to the mixer 124 via a wiring 122a, and the feeder 118 is connected to the mixer 124 via a wiring 122b. An output of the mixer 124 is connected to the pipeline 102. The mixer 124 mixes the medium 116 with the cell suspension 120, dilutes the cell to a concentration suitable for the injection, and feeds the cells to the injector 140 via the pipeline 102. Commands of the controller 112 can adjust the supplied fluid amounts and fluid pressure of the medium 116 and cell suspension 120, and thereby control the concentration of the cell suspension 120 output from the mixer 124. In the instant embodiment as described later, the feed controlling apparatus 130 feeds the cells C one by one to the injector 140: The concentration control is important because the excessively high cell concentration causes aggregation and the excessively low cell concentration reduces the throughput.

The concentration of cell suspension 120 filled in the feeder 118 is, for example, about $10^6$ cells/mL, which is a general concentration of the cell suspension where cells are incubated for several days after passage. As the cell suspension 120 is diluted by about 100 times at the mixer 124, the suspension of about $10^4$ cells/mL can be obtained. The controller 112 can use, but not exclusively, a well-known fluid feeder for the liquid chromatography. In the preferred embodiment, if the fluid supplying amount from the first feeder 110 is about 1 µL/min, each injector 140's performance is 10 cells/min when converted from the cell suspension concentration.

The feed controlling apparatus 130 controls feeding of plural cells that float in the fluid, to the injecting position for the injector 140. More specifically, the feed controlling apparatus 130 supplies the cells C one by one to the injector 140, and stops supplying the cells when the injector 140 provides the cell with the injection process. In FIG. 1, the feed controlling apparatus 130 is provided in the injector 140, but may be provided between the first feeder 110 and the injector 140. Without the feed controlling apparatus 130, the timings of flowing the cells C cannot be controlled and the following problems would occur: Plural cells are supplied to the predetermined position simultaneously; one cell collides with another cell that is being processed, obstructs the processing; and the cell to which the process has not yet completed (or the outstanding cell) flows downward due to the impact of the collision. The feed controlling apparatus 130 solves these problems.

Figure 2:
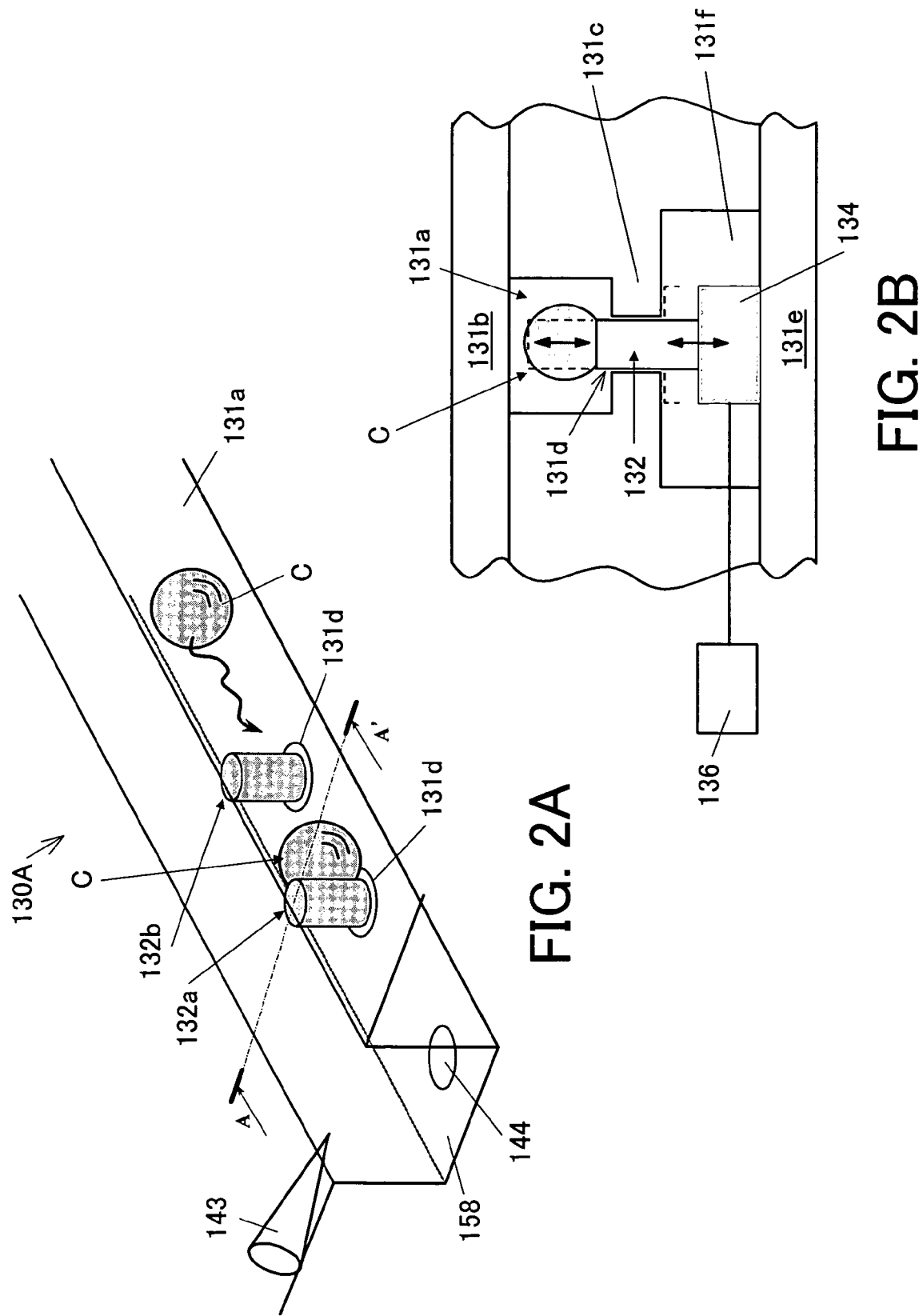
FIGS. 2A and 2B are schematic perspective and sectional views of a feed controlling apparatus and an injector in the cell processing system shown in FIG. 1.

Referring now to FIG. 2, a description will be given of the feed controlling apparatus 130A of the first embodiment. Here, FIG. 2A is a schematic perspective view of the feed controlling apparatus 130A. FIG. 2B is a sectional view taken along line A-A' in FIG. 2A. The feed controlling apparatus 130A includes a channel 131a, a pair of gates 132a and 132b (where the reference numeral 132 generalizes the reference numeral 132a, etc.), a gate drive unit 134 that drives each gate 132, and a controller 136. In FIG. 2, the cell C is graphically spherical.

The channel (or a micro-channel) 131a has such a width that allows the cells C to flow one by one, and restricts the flow directions of the cells C. Thereby, plural cells are prevented from being simultaneously supplied to the injecting position for the injector 140. The channel 131a is connected to the pipeline 102 and the channel 158. The pipeline 102 and the channel 131a may have the same structure or the pipeline 102 may be wider than the channel 131a. As shown in FIG. 2B, a top cover 131b defines the top of the channel 131a. A diaphragm 131c defines the side and the bottom of the channel 131a. The diaphragm 131c has a convex section in this embodiment, but the side and the bottom of the channel 131a may be comprised of different members. In this embodiment, if the cell C has a diameter, for example, of 15 to 25 µm, the channel has a width and height of 30 to 50 µm. The diaphragm 131c has a pair of holes 131d as shown in FIG. 2A.

A pair of gates 132 are provided in a pair of holes 131d in the diaphragm 131c, and displace (or move longitudinally) between a retreating (or opening) state and a projecting (or closing) state. In the embodiment shown in FIGS. 2A and 2B, only one cell can be housed between the gates 132a and 132b. In this embodiment, each gate 132 illustratively has a cylinder (or pile) shape having a diameter of about 20 µm. However, two or more gates may be provided along a flow direction of the channel like gates 133, which will be described later.

The gate 132 allows the cell C to flow along the channel 131a when it is in the retreating state, and prevents the cell C from flowing along the channel 131a when it is in the projecting state. The gates 132a and 132b operate separately and independently. If the gate 132 is made of metal, metallic ions dissolve in and contaminate the fluid. Therefore, it is made, for example, of ceramics and plastics. A clearance between the gate 132 and the hole 131d is set to be so minimum that even when the gate 132 moves, the fluid does not leak into the hole 131d.

The drive unit 134 drives the gate 132. The drive unit 134 uses, for example, a piezoelectric element, but may employ a solenoid and any known structures in the art. The piezoelectric element is suitable for fast movements of the gate 132. The drive unit 134 turns, when electrified, to a state shown in FIG. 2A, or a state shown by a dotted line in FIG. 2B, whereby the gate 132 turns to the projecting state. On the other hand, the drive unit 134 turns, when the electricity is released, to a state shown by a solid line in FIG. 2B, whereby the gate 132 turns to the retreating state. A switching speed between the projection and the retreat is sufficiently high in this embodiment. If the switching speed is adjustable, it is preferable to determine the switching speed based on the flow velocity of the fluid and object's concentration in the fluid so that the gate does not crush the cell.

Figure 3:
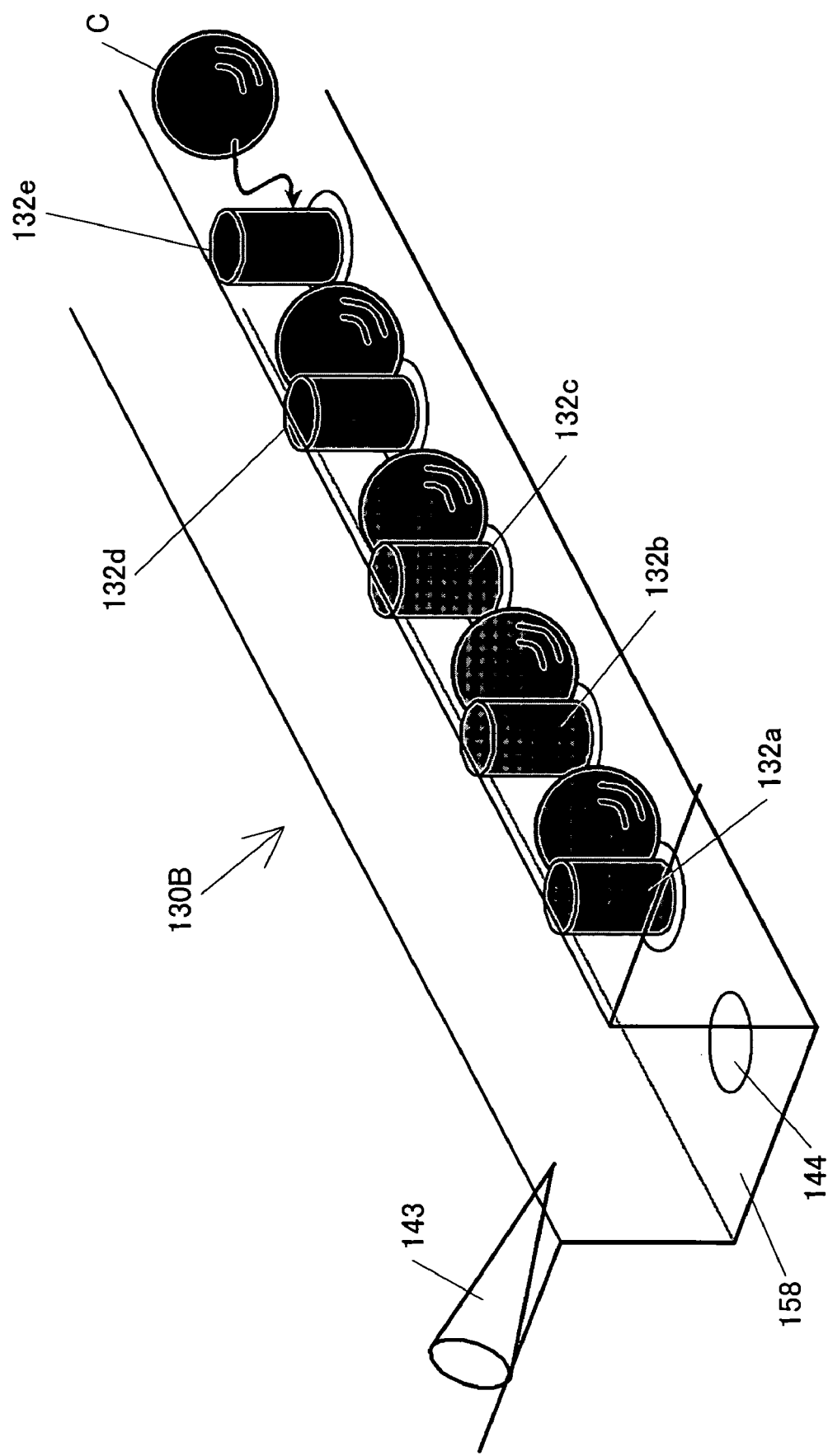
FIG. 3 is a schematic perspective view of a variation of the feed controlling apparatus shown in FIGS. 2A and 2B.

As shown in FIG. 3, the number of gates 132 is not limited to two as in this embodiment. Here, FIG. 3 is a schematic perspective view showing a feed controlling apparatus 130B having more gates 132a to 132e. The multi-gate structure shown in FIG. 3 can put plural cells on standby one by one along the channel 131a, and form a waiting line of the cells. A production of the continuous waiting line of the cells C enables the cells C to be processed continuously at regular time intervals. The cell concentration in the channel 131a is not necessarily constant. If the cells C can be slow to reach the injecting position or plural cells C reach the injecting position at the same time, the injecting process does not have regular time intervals or the throughput can lower. On the other hand, if plural cells C can be put on standby as shown in FIG. 3, for example, the injection and a formation of the waiting line can be conducted simultaneously and the process efficiency improves.

Turning back to FIG. 2, the gate 132a is arranged at the upstream side closest to the injecting position by the injector 140, which is a vacuum port 144 for capture of the cell in this embodiment. The gate 132 in the projecting state prevents the cell C's flow but permits the fluid's passage. This fluid's flow always creates a force to move the cells C downstream, and enables the gate to serve as a cell capture means, as discussed later.

The diaphragm 131c has a drive unit housing 131f as shown in FIG. 2B. The top and the side of the drive unit housing 131f are defined by the diaphragm 131c and the bottom is defined by a lower cover 131e. The drive unit housing 131f houses the drive unit 134.

The controller 136 communicates with a host controller 141 shown in FIG. 1, and controls the electrification to the drive unit 134. The host controller 141 may serve as the controller 136.

Figure 4:
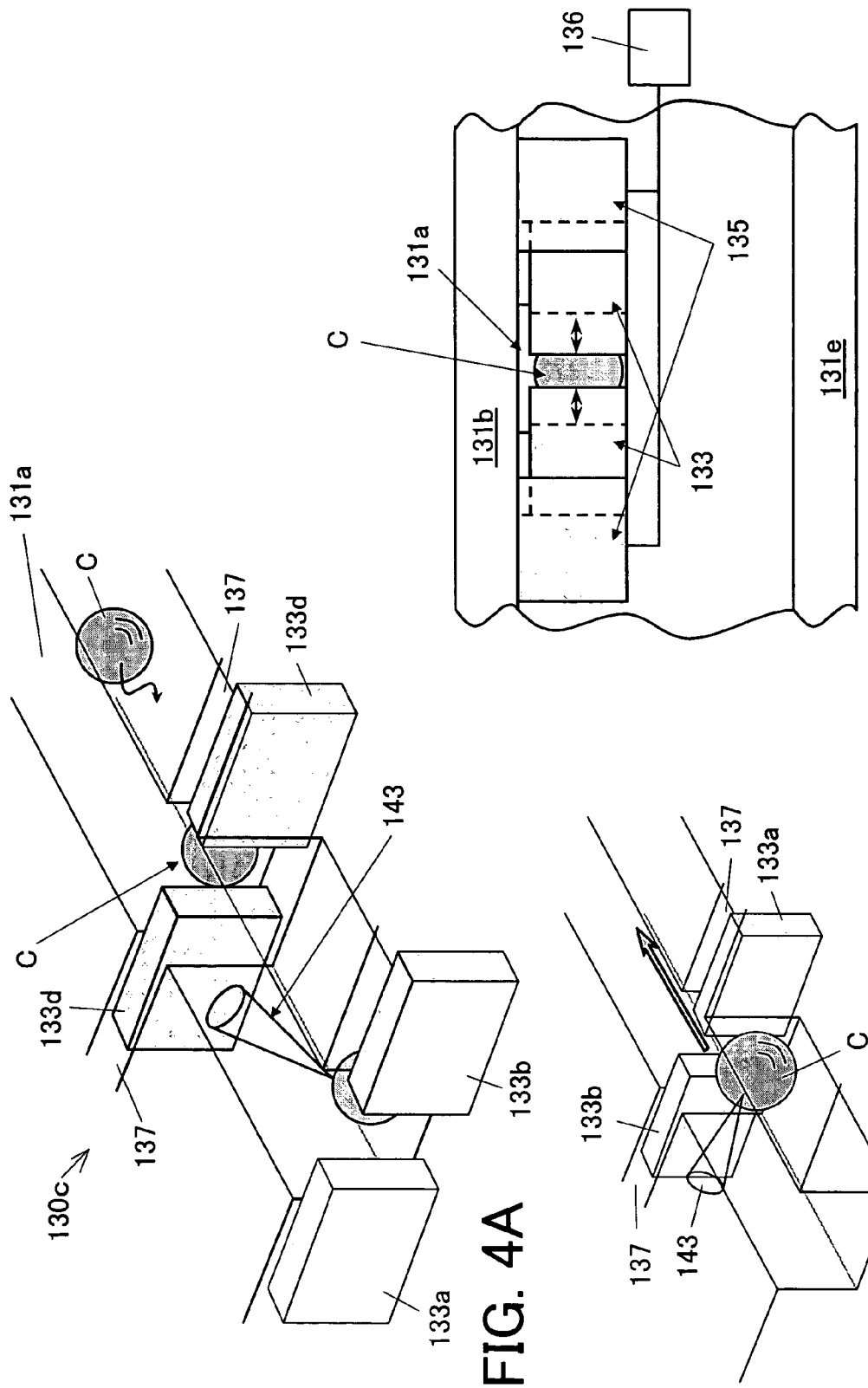
FIGS. 4A, 4B and 4C are schematic perspective and sectional views of another variation of the feed controlling apparatus and injector shown in FIGS. 2A and 2B.

Referring now to FIG. 4, a description will be given of the feed controlling apparatus 130C of a second embodiment. Here, FIG. 4A is a schematic perspective view of the feed controlling apparatus 130C. FIG. 4B is a schematic perspective view of gates 133a and 133b in the feed controlling apparatus 130 from an upstream direction. FIG. 4C is a transparent plane view for explaining driving of the gate 133. The reference numeral 133 generalizes 133a, etc.

The feed controlling apparatus 130C has a pair of double acting type gates 133a/133b and 133c/133d, and a drive unit 135 connected to the gate element of each gate. Each gate element 133 is movable along a groove 137 that is provided perpendicular to the channel. A clearance between each gate element 133 and the groove 137 is minute, and the fluid does not leak from the channel to the groove 137 in this embodiment. Which a moving direction of the gate element 133 is perpendicular to the channel 131a in the instant embodiment, the present invention is not limited to this embodiment. A size, arrangement and shape of the gate element 133 shown in FIG. 4 are also illustrative.

The gate 133a/133b allows and prohibits the feeding of the cell C along the channel 131a, and also serves as the cell capturing means. In other words, as the gate 133a/133b slightly opens at the time of attraction as shown in FIGS. 4B and 4C, the fluid can pass but the cell C cannot pass. As a result of that the fluid flows downstream, the cell C always receives a downstream force, and the cell C can be held between the gate elements 133a and 133b.

The drive unit 135 moves each gate element 133 along the groove 137. The drive unit 135 uses, for example, a piezoelectric element, but may employ a solenoid and any known structures in the art. The piezoelectric element is suitable for fast actions of the gate element 133. The drive unit 135 turns, when electrified, to a state shown by a solid line in FIG. 4C. In addition, the gate 133 turns to the projecting (or closing) state, allowing the fluid to pass but prohibiting the cell C from passing. An interval of the gate 133 is, for example, 5 μm to 10 μm. On the other hand, the drive unit 135 turns, when the electricity is released, to a state shown by a broken line in FIG. 4C. In addition, the gate 133 turns to the retreating (or opening) state. As a result, the cell C can pass between a pair of the gate elements. As discussed with reference to FIG. 3, the number of gates 133 is not limited.

The injector 140 injects gene and medication solutions into the cell. The injector 140 is arranged between the feed controlling apparatuses 130 and 160, and includes a host controller 141, an injection controller 142, a capillary 143, a vacuum port 144, a capture controller 145, a capture member 146, and a cell observer 150.

The host controller 141 communicates with and controls the controller 136, injection controller 142 and capture controller 145. The host controller 141 also communicates with and controls the controllers 161 and 171, which will be described later. The host controller 141 may be a CPU, a MPU and other controllers irrespective of its name, and includes one or more of the above controllers if necessary. As described later with reference to FIG. 13, the host controller 141 instructs the capture controller 145 to start a capture, when receiving a detection signal of the cell C from the cell observer 150. The host controller 141 instructs the injection controller 142 to start an injection, when receiving a capture completion signal from the cell observer 150. The host controller 141 instructs the capture controller 145 to release the capture so as to enable the cell to flow to the feed controlling apparatus 160, when receiving an injection completion signal from the injection controller 142. As described later with reference to FIG. 6, the host controller 141 (or injection controller 142) instructs the controller 136 to start an injection process, when communicating with and receiving a ready signal from the controller 136. The host controller 141 can independently process a large amount of cells C without manual operations.

The injection controller 142 drives the capillary 143 by controlling a timing, an injecting amount, angle and depth when the capillary 143 injects the gene and medication solutions into the cells C. A drive unit for the capillary 143 may be integrated with the capillary 143 in FIG. 1 or with the injection controller 142. The capillary 143 pierces into the cell membrane of the cell C, and injects the gene and medication solutions into the cell C. As one example, the capillary 143 projects into and retreats from the channel 158 via an opening 131g provided in a top cover 131b shown in FIG. 5, which will be described later. The capillary 143 has a sharp tip enough to pierce the cell, and its diameter is, for example, about 1 μm. The opening 131g, through which has the capillary 143 passes, has a diameter, for example, of about 10 μm to 20 μm. Such an injection approach can improve the success rate of the injection without restricting a combination between a cell and an introduced material.

Figure 5:
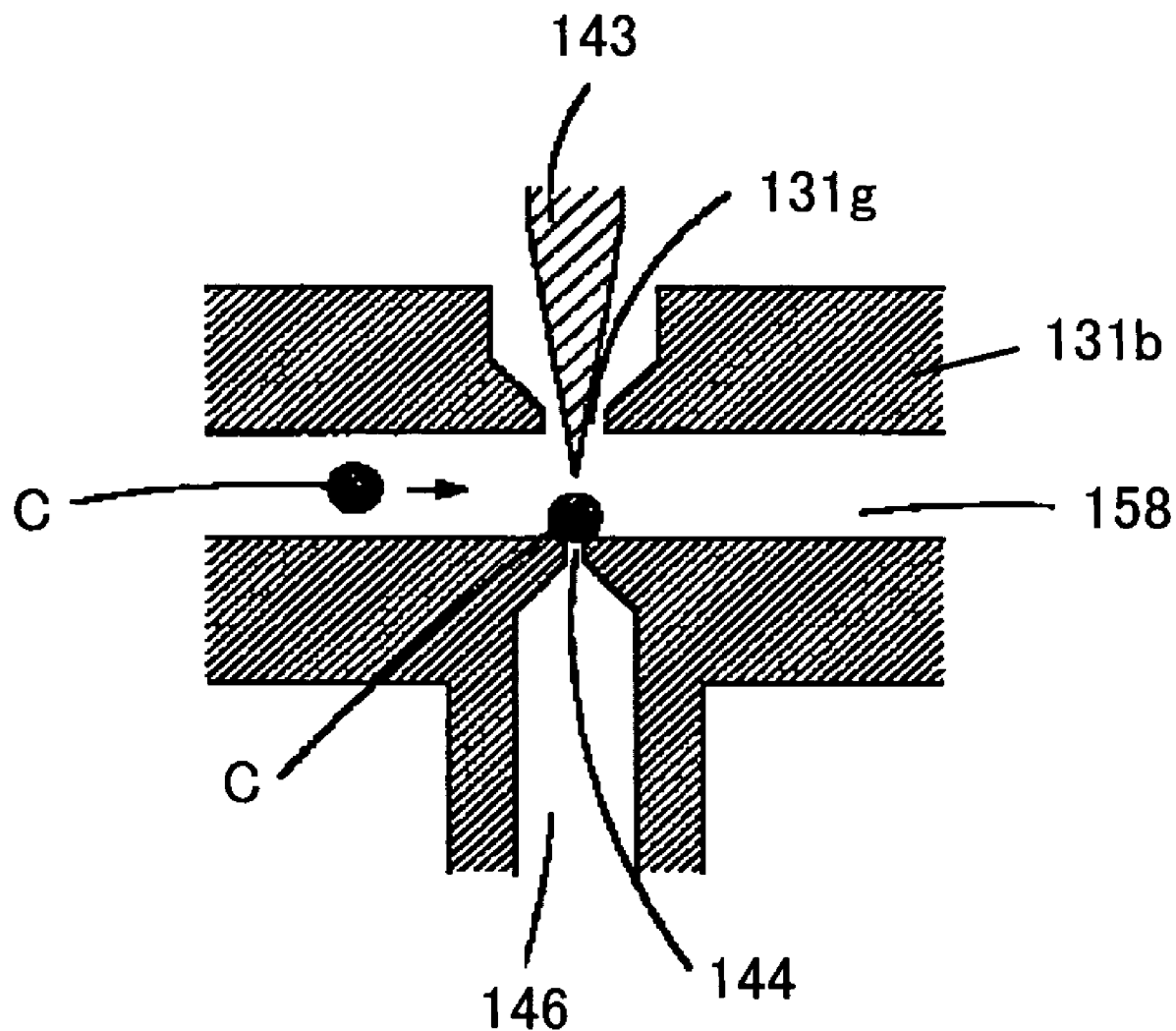
FIG. 5 is a schematic sectional view of the injector shown in FIGS. 2A and 2B.

The vacuum port 144 is a hole in connected to the channel 131a, which is provided at a predetermined position of the diaphragm 131c as shown in FIGS. 2A and 3. The vacuum port 144 serves to fix only one cell C, and is provided in the bottom surface of the channel 158 in FIGS. 2A and 3 but may be provided in the side or another surface. The capture controller 145 controls a fixing action of the cell C by the capture member 146. More specifically, the capture controller 145 in the instant embodiment controls the capturing pressure and time by the capture member 146 when the capture member 146 fixes the cell C. While the capture member 146 in this embodiment applies the negative pressure to the vacuum port 144 to fix the cell C in the vacuum port (at the predetermined position), the present invention does not limit the fixing method of the cell C. For example, a capture unit that can be driven by a piezoelectric element, etc. may be connected so as to mechanically capture the cell C or a cell affinity material may be used to capture the cell. The capture member 146, for example, has a structure shown in FIG. 5 in this embodiment. Here, FIG. 5 is a schematic enlarged sectional view of part A in FIG. 1, in which the vacuum port 144 having about Φ several micrometers attracts the fluid in the channel 158 and the cell C to capture the cell C. According to the automated feeding of the cells to be injected in this embodiment by feeding the cell and by capturing the cell using the capture member 146, a large amount of cells are injected with good throughput and workability, without manual operations on the laboratory dish as in the prior art.

The cell observer 150 serves to observe an injection operation to the cell C, and includes an image processor 152, an objective lens 154, a light source 156 and a channel 158. The objective lens 154 and the light source 156 form a microscope. The image processor 152 includes an image pickup unit, such as a CCD, and a processor that processes an output from the CCD. The image processor 152 photographs and image-processes the inflows of the cell C to the channels 131a and 158, its capture and injection states under the microscope field, as well as communicating with the host controller 141. More specifically, the image processor 152 always observes and monitors the channels 131a and 158, and sends to the host controller 141 a detection signal of the cell C, a signal indicative of capture completion of the cell C by the capture member 146, and a signal indicative of injection completion. The cell observer 150 communicates with the controller 136 and informs the controller 136 of whether the cell C is filled in a space or buffer between two adjacent gates, as described later with reference to FIGS. 7 and 8. The channel 158 has a width enough to flow the cells C one by one, similar to the channel 131a, and is connected to the channel 131a and the pipeline 102. The channel 158 is arranged under the field of the microscope that includes the light source 156 and the objective lens 154. The channel 158 is composed of a transparent member so as to observe actions of the cell C in the channel.

The feed controlling apparatus 160 has three major functions in this embodiment. However, the feed controlling apparatus 160 does not always have to possess these three functions according to the present invention. The feed controlling apparatus 160 that serves as the first function will suffice. According to the first function, the feed controlling apparatus 160 guides, based on whether the injection by the injector 140 has succeeded or failed, only the successfully injected cells to a channel to the dispenser unit 180 (or the pipeline 177b), and other cells to the channel 168 to a collection container 169. The channel 168 is connected to the collection container 169 that collects cells to be disposed. While FIG. 1 arranges the feed controlling apparatus 160 in the second feed controlling apparatus 170, the feed controlling apparatus 160 may be provided between the injector 140 and the second feed controlling apparatus 170. While FIG. 1 arranges the feed controlling apparatus 160 in front of the mixer 178 to enhance the first function, but the feed controlling apparatus 160 may cover the mixer 178 so as to implement the second and third functions.

Figure 9:
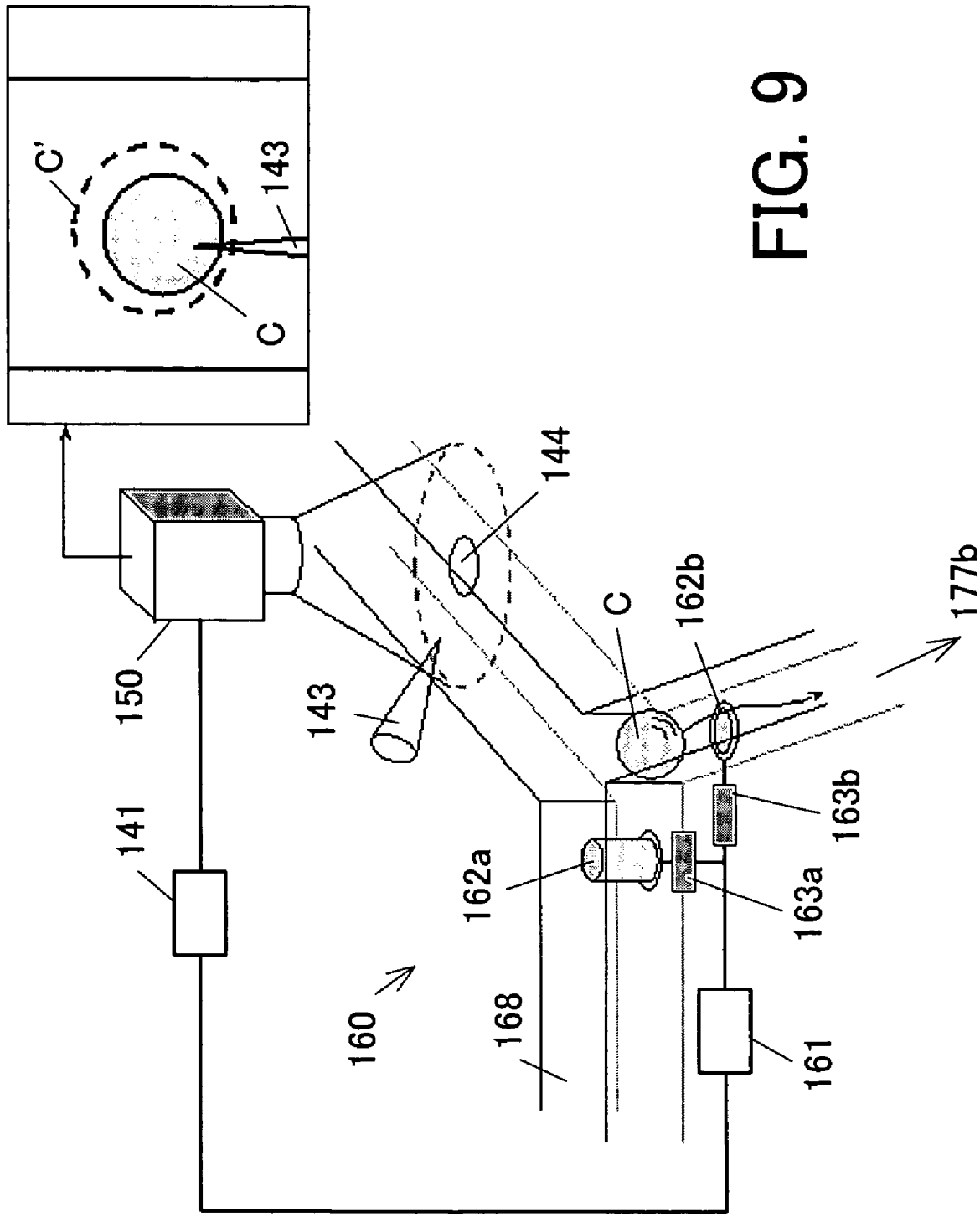
FIG. 9 is a schematic perspective view showing the injector and another feed controlling apparatus (or a sorter) in the cell processing system shown in FIG. 1.

As shown in FIG. 9, the feed controlling apparatus 160 has a controller 161 that communicates with the host controller 141 (or the image processor 152), and gates 162a and 162b in order to implement the first function. Here, FIG. 9 is a schematic perspective view of the feed controlling apparatus 160. The controller 161 communicates with the host controller 141, executes the process shown in FIG. 10, and opens a channel to the dispenser unit 180 for the successfully injected cells C by changing the gate 162a to the projecting (or closing) state and the gate 162b to the retreating (or opening) state as shown in FIG. 9. On the other hand, the controller 161 opens a channel 168 to the collection container 169 for other cells C by changing the gate 166 to the projecting (or closing) state and the gate 162a to the retreating (or opening) state.

According to the structure shown in FIG. 9, the feed controlling apparatus 160 can provide the dispenser unit 180 with only successfully injected cells C and improve the analysis precision. For example, in analyzing the expression rate of the cells C, defective cells if erroneously mixed would deteriorate the analysis and evaluation precisions. The cells would also become defective if the feed controlling apparatus 130 erroneously supplies two cells to the capillary 143 simultaneously or if the cell C blows up at the time of injection even if the feed controlling apparatus 130 supplies the cells C one by one to the capillary 143. The feed controlling apparatus 160 solves these problems.

According to the second function, the feed controlling apparatus 160 calculates the success rate and the continuous failure number of the injections by the injector 140 in cooperation with the host controller 141, monitors whether the injector 140 normally operates, and immediately warns an operator when determining that it is abnormal. In order to implement the second function, the feed controlling apparatus 160 connects counters 163a and 163b to the gates 162a and 162b, in addition to the controller 161, as shown in FIG. 9. The counter 163a counts the number of changes of the gate 162a from the projecting state to the retreating state. The gate 162b counts the number of changes of the gate 162b from the projecting state to the retreating state.

Information of the counters 163a and 163b is sent to the controller 161, and the controller 161 calculates the injection success rate and the continuous failure number of the injections by the injector 140. The controller 161 may simply send the information of the counters 163a and 163b to the host controller 141, and the host controller 141 may calculate the above values. When the host controller 141 obtains the injection success rate and the continuous failure number of the injector 140, compares them with predetermined thresholds, and warns the operator when they are lower than the predetermined thresholds via a lamp or speaker (not shown).

Figure 11:
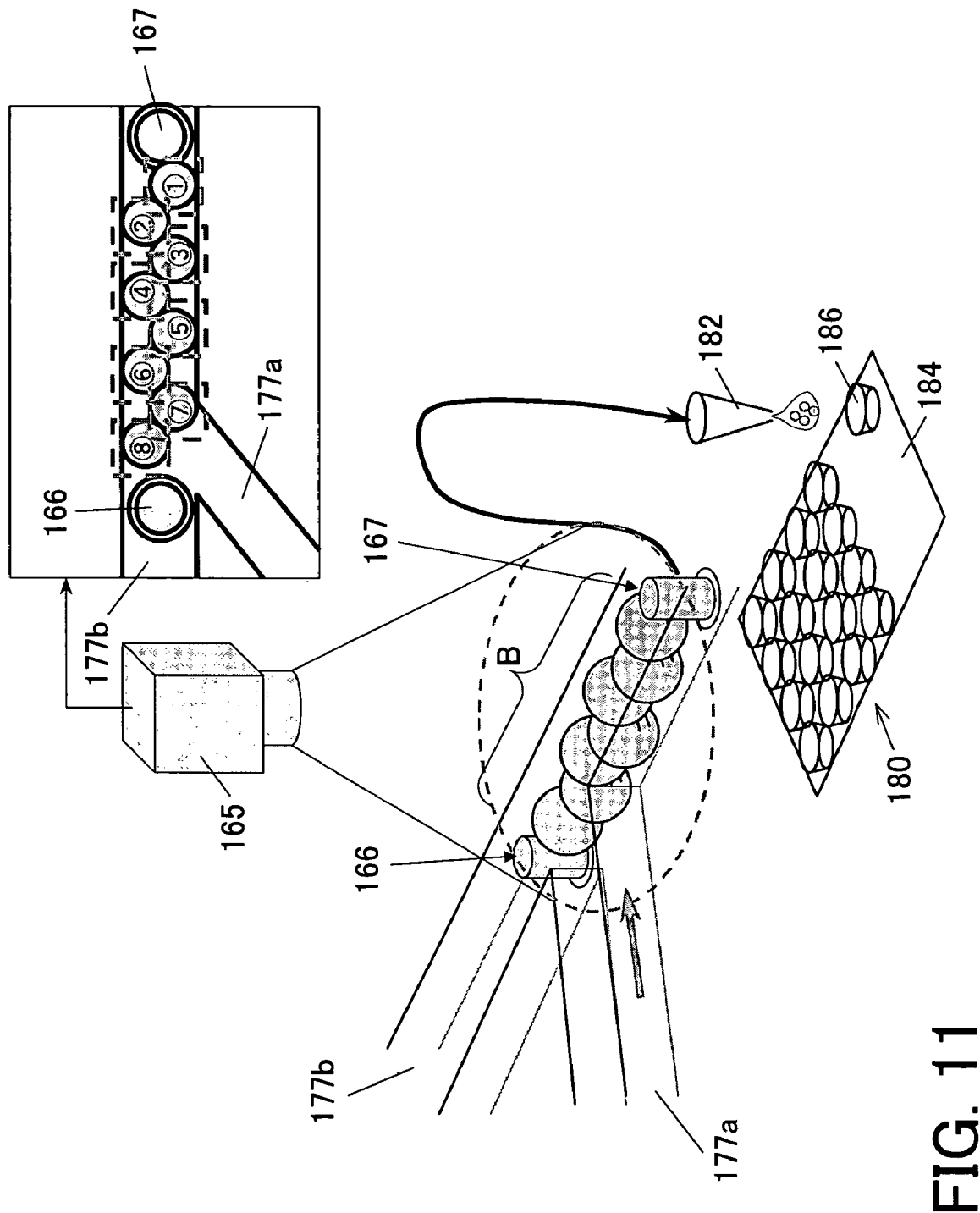
FIG. 11 is a schematic perspective and plane view of other components in the feed controlling apparatus shown in FIG. 9 and a dispenser shown in FIG. 1.

According to the third function, the feed controlling apparatus 160 stores a predetermined amount of injected cells, and simultaneously supplies the stored cells to the dispenser unit 180. In order to implement the third function, the feed controlling apparatus 160 further includes, as shown in FIG. 11, an image processor 165 and gates 166 and 167 in addition to the controller 161. Here, FIG. 11 is a schematic perspective view of a structure near the mixer 178 of the feed controlling apparatus 160. The image processor 165 is configured similar to the image processor 150, and photographs the storage state of the cells C near the mixer 178. The gate 166 serves to prevent the backflow of the cells C, and the gate 167 controls sending of the cells C.

According to the structure shown in FIG. 11, the feed controlling apparatus 160 serves to supply the cells to the dispenser unit 180 and assists the dispenser unit 180 in the subsequent process. In other words, a volume near one cell is several tens picoliters, and does not always form a drop depending upon the viscosity of the medium. A predetermined concentration, for which only one cell is insufficient, is needed for divisions and culture in the dispenser unit 180. The feed controlling apparatus 160 can store a predetermined number (eight in FIG. 11) of cells C between the gates 166 and 167, and solves this problem.

As shown in FIG. 11, the controller 161 turns the gate 167 to the retreating state and supplies the cells C to the dispenser unit 180, only when determining that a predetermined number of successfully injected cells C are stored between the gates 166 and 167. The controller 161's determination is based on an output of the image processor 165 and/or the number of openings of the gate 162b. While FIG. 11 shows that eight cells are put on standby between the gates 166 and 167 and simultaneously supplied to the incubator 186, the present invention neither limits the number of stored cells, nor requires the storable number of cells between the gates 166 and 167 to be always equal to the number of cells to be simultaneously supplied to the incubator 186.

The second feeding unit 170 is located at the downstream side of the feed controlling apparatus 160, and feeds the injected cells. The second feeding unit 170 includes a controller 172, a supplier 174 and the mixer 178. The supplier 174 supplies the medium 176. The controller 172 controls supplying of the supplier 174. The supplier 174 is connected to the mixer 178 via a pipeline 177a, and the feed controlling apparatus 160 is connected to the mixer 178 via a pipeline 177b. The mixer 178 is connected to a pipeline 179. The mixer 178 mixes the medium 176 with the cell suspension that contains the injected cells, dilutes the cells C to a suitable concentration, and feeds the cells to the injector 180 via the pipeline 179. The controller 172's instruction can adjust the fluid supply amount and fluid pressure of the medium 174 and the injected cell. This structure controls the concentration of the suspension output from the mixer 178. The cell suspension 120 contains the cells C and the fluid, and that fluid is also supplied to the mixer 178 but the amount is so small that the controller 172 in the instant embodiment ignores the fluid amount. While the cells are put on standby by the third function of the feed controlling apparatus 160, the fluid contained in the cell suspension 120 is prevented from being supplied to the incubator 186. Alternatively, the controller 172 may determine the amount of the medium 176 by considering the fluid amount contained in the cell suspension 120 supplied to the pipeline 179. As a result, each incubator 186 in the dispenser unit 180 is provided with the predetermined concentration of cells.

The dispenser unit 180 serves to dispense individual cells in the diluted cell suspension that contains the injected cells, into a universal multi-hole plate, and may use a known fluid dispenser. As shown in FIG. 11, the dispenser unit 180 includes a nozzle 182, a plate 184 and the incubators 186. The plate 184 has many holes, and the incubator 186 is set in each hole. The feed controlling apparatus 160 enables the nozzle 182 to simultaneously supply a predetermined number of cells C to the incubator 186. Thereby, the cells can be stored in a treatable unit, and it is then possible to confirm the cloning of the cell and effect expressions of introduced gene and medication, if necessary. The analysis precision improves, since the feed controlling apparatus 160 feeds only the successfully injected cells to the dispenser unit 180.

Figure 6:
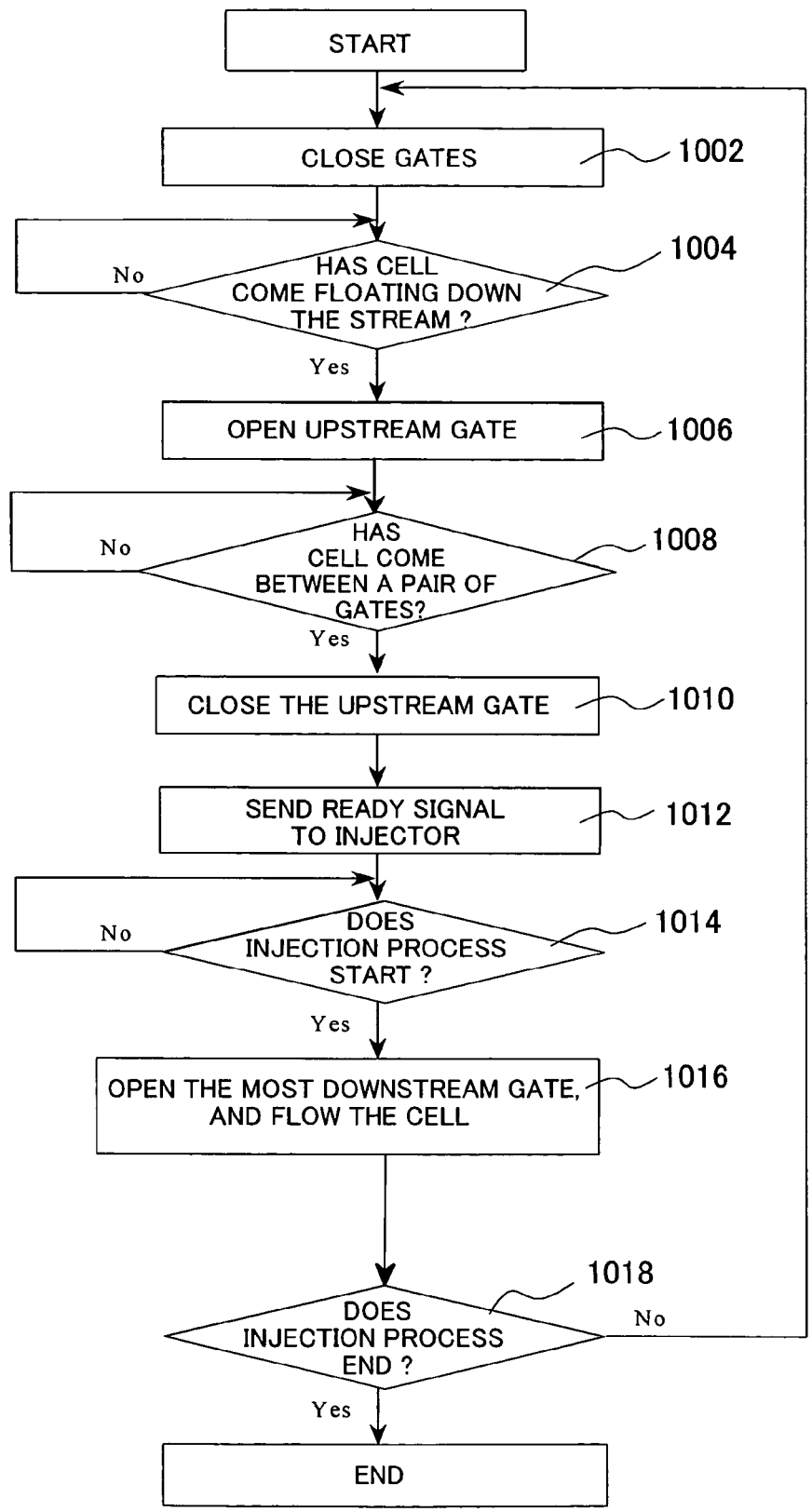
FIG. 6 is a flowchart for explaining an operation of the feed controlling apparatus shown in FIGS. 2A and 2B.

Referring now to FIG. 6, a description will be given of the operations of the feed controlling apparatus 130A. Here, FIG. 6 is a flowchart showing a feed controlling method by the controller 136 in the feed controlling apparatus 130A. First, the controller 136 electrifies the drive unit 134 and turns the gates 132a and 132b to the projecting states (step 1002). Next, the controller 136 communicates with the host controller 141 (or the cell observer 150), and determines whether the cell C comes floating down the stream (step 1004). The controller 136 repeats the step 1004 until the controller 136 determines that the cell flows down. When determining that the cell has flowed down (step 1004), the controller 136 releases the electrification to the drive unit 134 and turns the gate 132b to the retreating position (step 1006).

Next, the controller 136 communicates with the host controller 141 (or the cell observer 150), and determines whether the cell C is filled in the space or buffer between gates 132 (step 1008). The controller 136 repeats the step 1008 until the cell C is filled in the space between the gates 132. The controller 136 electrifies the drive unit 134 and changes the gate 132b to the projecting position when determining that the cell C is filled in the space between gates 132 (step 1010). As a result, one cell C is held between the gates 132, as shown in FIG. 2A.

Next, the controller 136 sends a ready signal to the host controller 141 (or the injection controller 142) (step 1012). Then, the controller 136 determines whether the controller 136 receives an injection start signal from the host controller 141 (or the injection controller 142) (step 1014). The controller 136 repeats the step 1014 until it receives the injection start signal. When determining that it has received the injection start signal (step 1014), the controller 136 releases the electrification to the drive unit 134 and changes the gate 132a to the retreating position (step 1016). As a result, the cell C flows to the injecting position for the capillary 143. Thereafter, the capillary 143 injects the gene and medication solutions into the cell C. Until the controller 136 receives from the host controller 141 (or the injection controller 142) a signal indicating that an injection process ends (step 1018), the controller 136 returns to the step 1002 after the step 1016. When receiving the injection process termination signal, the controller 136 terminates the feed controlling process.

Figure 7:
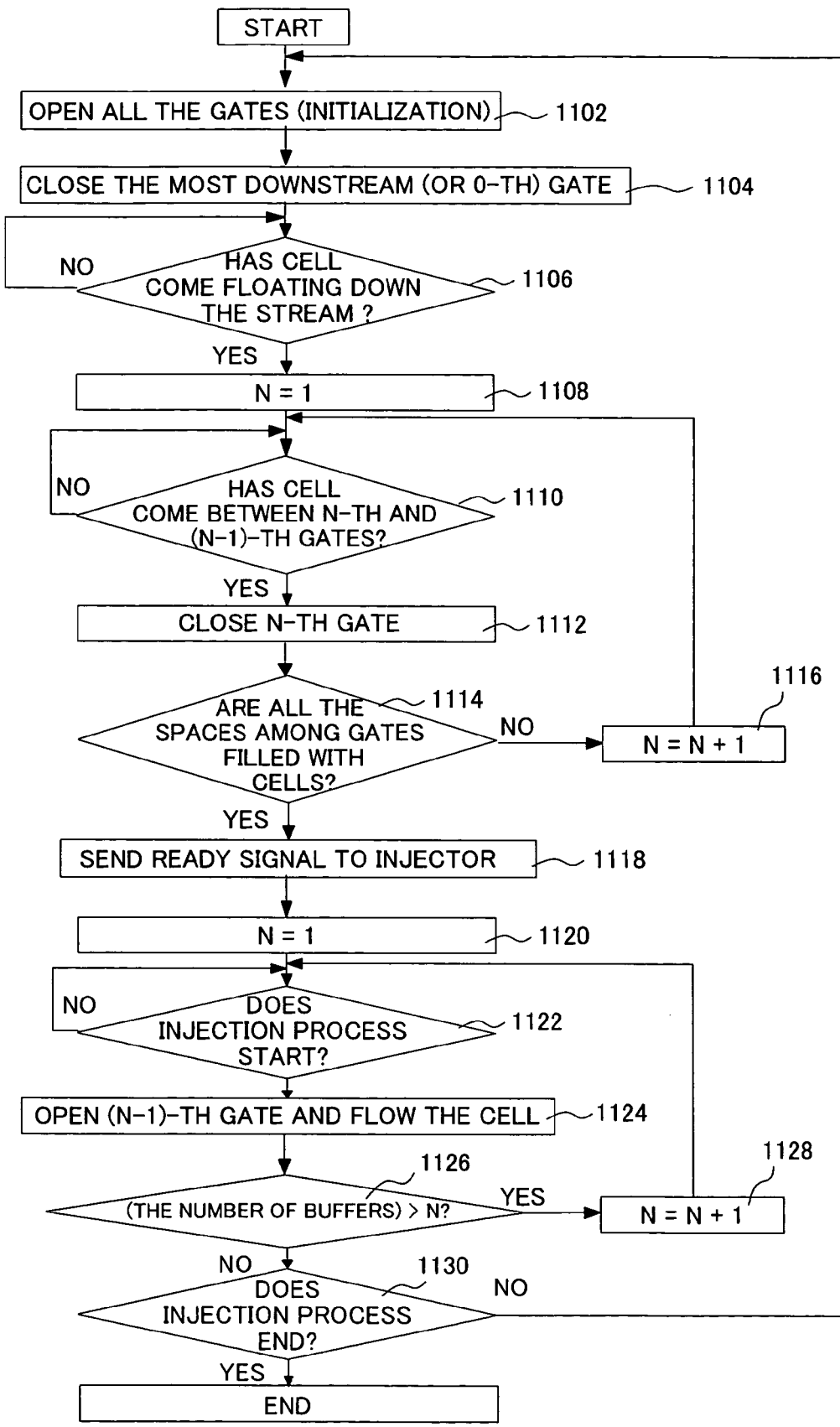
FIG. 7 is a flowchart for explaining an operation of the feed controlling apparatus shown in FIG. 3.

Referring now to FIG. 7, a description will be given of an operation of the feed controlling apparatus 130B. Here, FIG. 7 is a flowchart showing a feed controlling method by the controller 136 in the feed controlling apparatus 130B. First, the controller 136 releases the electrifications to all the drive units 134 and opens the gates 132 (step 1102). Next, the controller 136 electrifies the drive unit 134 to change the gate 132a to the projecting state (step 1104). Then, the controller 136 communicates with the host controller 141 (or the cell observer 150), and determines whether the cell C comes floating down the stream (step 1106). The controller 136 repeats the step 1106 until determining that the cell flows down. When the controller 136 determines that the cell has flowed down (step 1106), the controller 136 sets N to 1 (step 1108).

Next, the controller 136 communicates with the host controller 141 (or the cell observer 150), and determines whether the cell C is held between a N-th gate and a (N−1) gate (step 1110). The controller 136 repeats the step 1110 until determining that the cell C is held between the N-th gate and the (N−1) gate. When determining that the cell C is held between the N-th gate and the (N−1) gate (step 1110), the controller 136 electrifies the drive unit 134 and changes the N-th gate 132 to the projecting position (step 1112). The controller 136 determines whether the cell C is held in each of all the spaces among the gates 132 (step 1114), and returns to the step 1110 by incrementing N=N+1 (step 1116) when the controller 136 determines that the cell C is not held in each of all the spaces among the gates 132.

On the other hand, when the controller 136 determines that the cell C is held in each of all the spaces among the gates 132 in the step 1114, the controller 136 sends a ready signal to the host controller 141 (or the injection controller 142) (step 1118), and sets N to 1 (step 1120). Then, the controller 136 determines whether the controller 136 receives an injection start signal from the host controller 141 (or the injection controller 142) (step 1122). The controller 136 repeats the step 1122 until it receives the injection start signal. When determining that it has received the injection start signal (step 1122), the controller 136 releases the electrification to the drive unit 134 and changes the (N−1)-th gate 132 to the retreating position (step 1124). As a result, the cell C flows to the injecting position. Thereafter, the capillary 143 injects the gene and medication solutions into the cell C.

Next, the controller 136 determines whether the total of the gates (or the number of buffers as a space for housing the cell between the gates) is greater than N (step 1126). The controller 136 moves to step 1128 when determining that it is greater and moves to step 1130 when determining that it is not greater. In the step 1128, the controller 136 sets N=N+1 and returns to the step 1122. In the step 1130, the controller 136 returns to the step 1102 until the controller 136 receives from the host controller 141 (or the injection controller 142) a signal indicating that an injection process ends (step 1018). In response to the injection process termination signal from the host controller 141, the controller 136 terminates the feed controlling process. An example shown in FIG. 7 indicates a process that supplements the cell C to a buffer after the cell C has been fed from the buffer.

Figure 8:
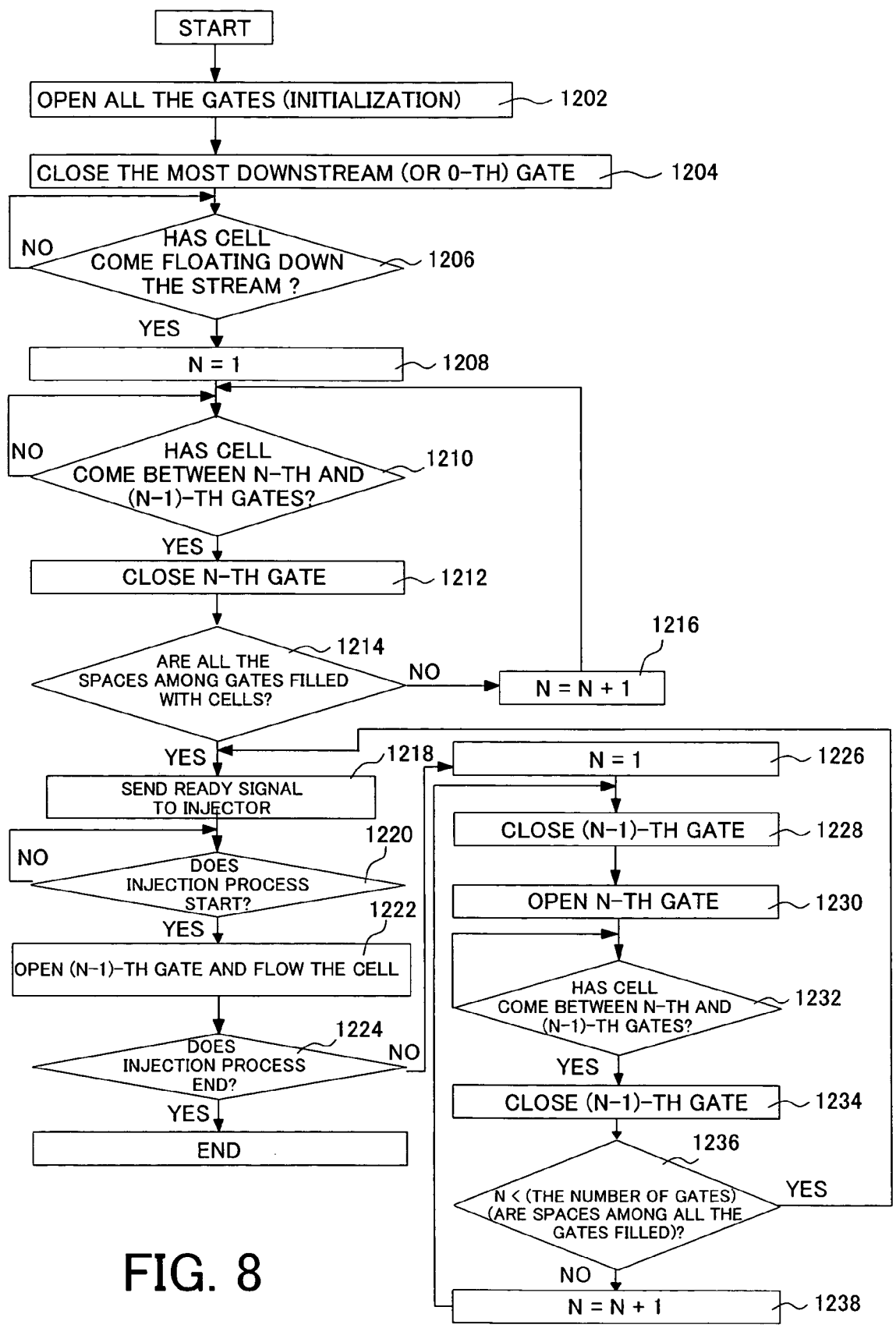
FIG. 8 is a flowchart for explaining another operation of the feed controlling apparatus shown in FIG. 3.

Referring now to FIG. 8, a description will be given of another operation of the feed controlling apparatus 130B. Here, FIG. 8 is a flowchart showing another feed controlling method by the controller 136 in the feed controlling apparatus 130B. First, the controller 136 releases the electrifications to all the drive units 134 and opens the gates 132 (step 1202). Next, the controller 136 electrifies the drive unit 134 to change the gate 132 to the projecting state (step 1204). Then, the controller 136 communicates with the host controller 141 (or the cell observer 150), and determines whether the cell C comes floating down the stream (step 1206). The controller 136 repeats the step 1206 until determining that the cell flows down. When the controller 136 determines that the cell has flowed down (step 1206), the controller 136 sets N to 1 (step 1208).

Next, the controller 136 communicates with the host controller 141 (or the cell observer 150), and determines whether the cell C is held between a N-th gate and a (N−1) gate (step 1210). The controller 136 repeats the step 1210 until determining that the cell C is held between the N-th gate and the (N−1) gate. When determining that the cell C is held between the N-th gate and the (N−1) gate (step 1210), the controller 136 electrifies the drive unit 134 and changes the N-th gate 132 to the projecting position (step 1212). The controller 136 determines whether the cell C is held in each of all the spaces among the gates 132 (step 1214), and returns to the step 1210 by incrementing N=N+1 (step 1216) if determining not.

On the other hand, if the controller 136 determines that the cell C is held in each of all the spaces among the gates 132 in the step 1214, the controller 136 sends a ready signal to the host controller 141 (or the injection controller 142) (step 1218). Then, the controller 136 determines whether the controller 136 receives an injection start signal from the host controller 141 (or the injection controller 142) (step 1220). The controller 136 repeats the step 1220 until it receives the injection start signal. When determining that it has received the injection start signal (step 1220), the controller 136 releases the electrification to the drive unit 134 and changes the gate 132a to the retreating position (step 1222). As a result, the cell C flows to the injecting position. Thereafter, the gene and medication solutions are injected into the cell C from the capillary 143. The controller 136 moves to step 1226 until receiving from the host controller 141 (or the injection controller 142) a signal that indicates that the injection process ends (step 1224). In response to the injection process termination signal, the controller 136 ends the feed controlling process.

In the step 1226, the controller 136 sets N=1, and then changes the (N−1)-th gate 132 to the projection state (step 1228). Next, the controller 136 changes the N-th gate 132 to the retreating state (step 1230). Next, the controller 136 communicates with the host controller 141 (or the cell observer 150), and determines whether the cell C is filled in the space between N-th and (N−1)-th gates (step 1232). The controller 136 repeats the step 1232 until the cell C is filled in the space between the N-th and (N−1)-th gates. When determining that the cell C is filled in the space between the N-th and (N−1)-th gates (step 1232), the controller 136 electrifies the drive unit 134 and changes the N-th gate 132 to the projecting position (step 1243). Next, the controller 136 determines whether the cell C is held in each of all the spaces among the gates 132 (step 1236). The controller 136 returns to the step 1218 if determining that the cell C is held, and moves to the step 1228 by incrementing N=N+1 (step 1238) if determining not.

Figure 10:
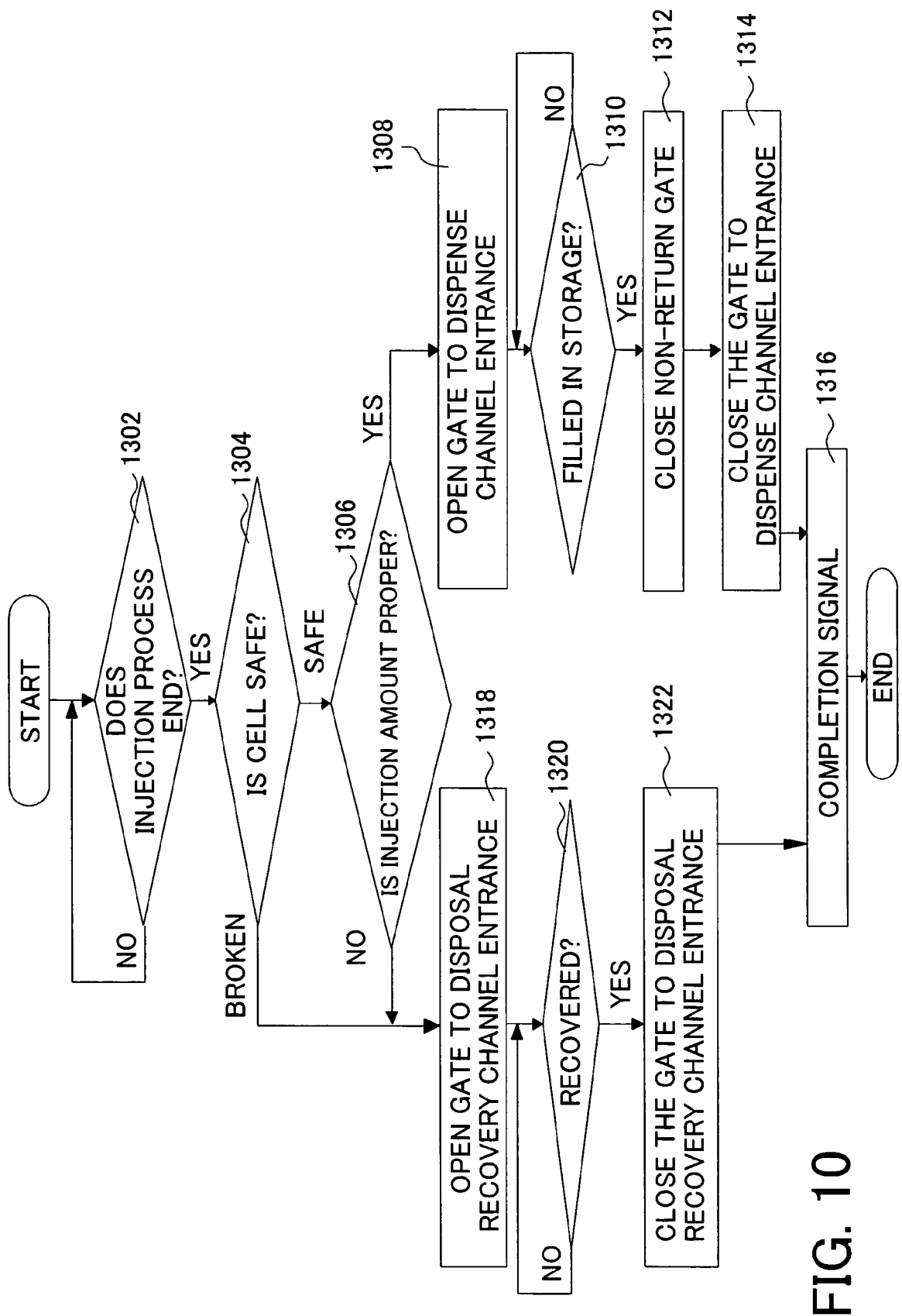
FIG. 10 is a flowchart for explaining an operation of the feed controlling apparatus shown in FIG. 9.

Referring now to FIG. 10, a description will be given of a feed controlling method by the controller 161 in the feed controlling apparatus 160. Here, FIG. 10 is a flowchart for explaining the feed controlling method by the feed controlling apparatus 160. First, the controller 161 communicates with the host controller 141 (or the cell observer 152), and determines whether the injection to the cell C (i.e., capture, and capillary 143's insertion and injection) completes (step 1302). The controller 161 repeats the step 1302 until the injection to the cell C completes. The controller 161 starts determining whether the injection has succeeded or failed, when the injection to the cell C completes (step 1302).

First, the controller 161 communicates with the host controller 141 (or the cell observer 150) and determines whether the cell C has broken based on upper right image information in FIG. 9 (step 1304). Next, the controller 161 determines whether the injecting amount to the cell C was proper based on information from the cell observer 150 (step 1306). More specifically, as shown in FIG. 9, the controller 161 determines whether a size of the cell C is within a permissible range that has a center of the size of the dotted line C' and covers ± several % of the size of the dotted line C' after the gene and medication are injected. When the controller 161 determines when the injecting amount is proper (step 1306), the controller 161 opens a channel to the dispenser unit 180 by turning the gate 162a to the projecting state and the gate 162b to the retreating state as shown in FIG. 9 (step 1308).

On the other hand, the controller 161 determines whether the cell C is stored in a storage B (step 1310). The controller 161 repeats the step 1310 until the cell C is stored in the storage B. When determining that the cell C is stored in the storage B (step 1310), the controller 161 closes the non-return gate 166 (step 1312). At the same time, the controller 161 turns the gate 162b to the projecting state (step 1314), and sends a completion signal to the host controller 141.

On the other hand, when determining that the cell was broken (step 1304) or the injecting amount was improper (step 1306), the controller 161 opens the channel 168 to the collection container 169 by turning the gate 162b to the projecting state and the gate 162a to the retreating state (step 1318). Next, the controller 161 determines whether the cell C is collected by the collection container 169 via the image processor 165 provided above the channel 168 (step 1320), and turns the gate 162a to the projecting state when determining that it has been collected (step 1322).

Figure 12:
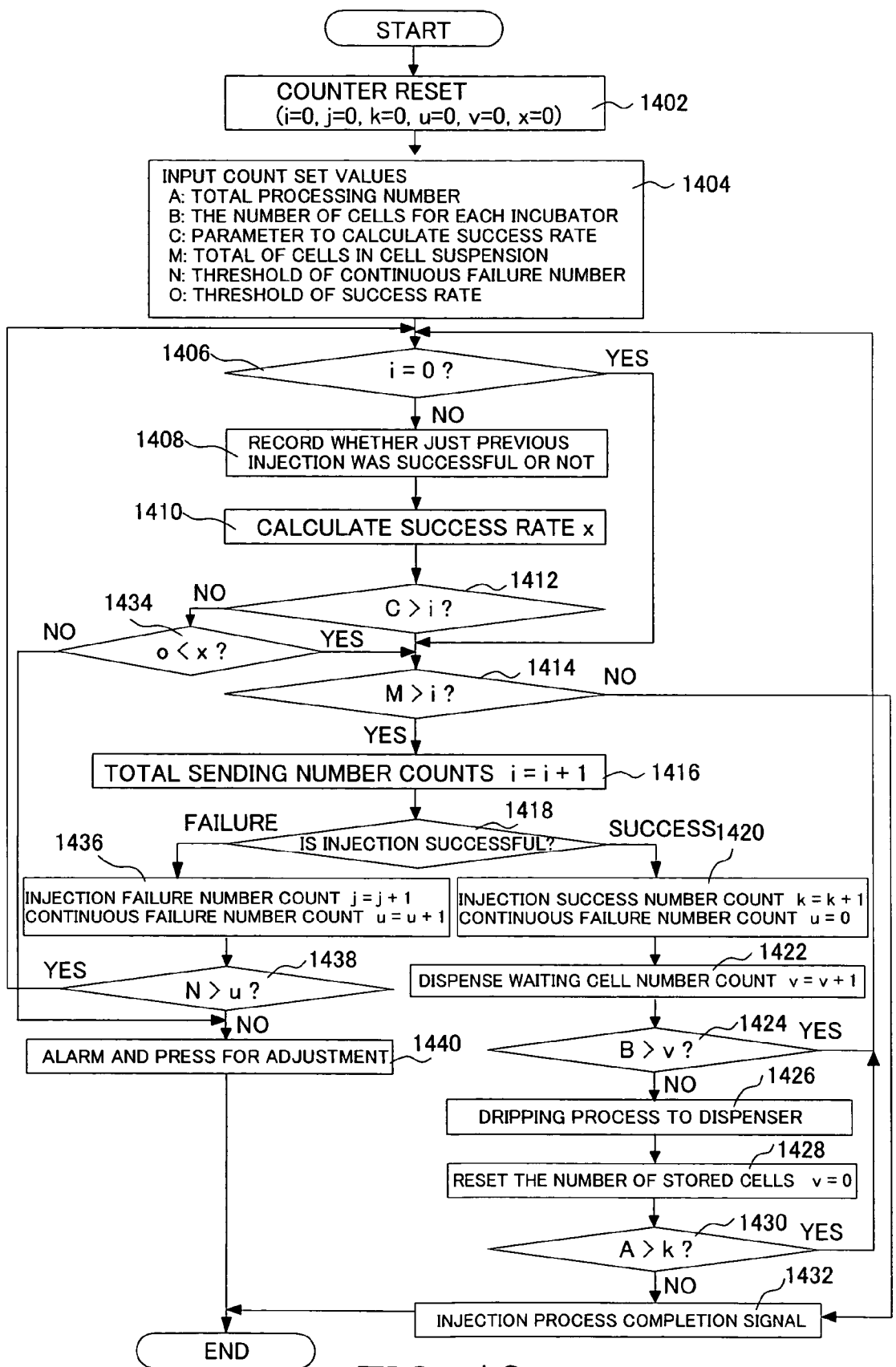
FIG. 12 is a flowchart for explaining an operation of the feed controlling apparatus shown in FIG. 11.

Referring now to FIG. 12, a description will be given of second and third functions of the feed controlling apparatus 160. Here, FIG. 12 is a flowchart for explaining another operation of the feed controlling apparatus 160. First, the controller 161 resets the counters and sets i=0, j=0, k=0, u=0, v=0 and x=0 (step 1402). "i" indicates the number of supplies of the cells to the injector 140. "j" indicates the number of unsuccessful injections. "k" indicates the number of successful injections. "u" indicates the number of continuously unsuccessful injections. "v" indicates the number of cells stored in the storage B (or the number of cells that are stored between the gates 166 and 167 and simultaneously supplied to each incubator 186). "x" indicates the success rate of the injection by the injector 140. Next, various set values are set (step 1404). The set objects in this embodiment include the total processing number "A", the number of cells for each incubator 186 "B", parameter to calculate success rate "C", the total of cells in the cell suspension 120 "M", the threshold in continuous failure number "N", and the threshold of success rate "O". The total processing number A is generally an integer multiple of B, which is the total of incubators 186.

Next, the controller 161 communicates with the host controller 141 and determines whether i=0 (step 1406). When determining that i is not 0 (step 1406), the controller 161 records the success of failure of the just previous injection (step 1408) and calculates the actual injection success rate x (step 1410). On the other hand, when determining that i is 0 (step 1406), the controller 161 moves to step 1414 since there was no injection process before.

When determining that i is not 0 (step 1406), the controller 161 determines whether the parameter C>the number of supplies i (step 1412). If C>i, the injector 140 has not yet processed the number of cells necessary to calculate the success rate. Then, the controller 161 determines whether the number of cells M>the number of supplies i (step 1414). If M>i, the cell suspension 120 contains the cell(s) to be processed. When determining that the number of cells M>the number of supplies i, the controller 161 communicates with the host controller 141 and increments i=i+1, as the host controller 141 turns the gate 132a to the retreating state (step 1416).

Next, the controller 161 determines whether the injection has succeeded (step 1418), and increments k=k+1 and resets u=0 (step 1420) if determining that the injection has succeeded. Next, the controller 161 increments v=v+1 (step 1422), and determines whether the number of cells B>the number of cells v (step 1422). If B>v, a necessary number of cells for each incubator 186 (or eight cells in FIG. 11) have not yet been stored between the gates 166 and 167 and thus the controller 161 returns to the step 1406. On the other hand, when determining that B is not greater than v, the controller 161 executes the dispenser dripping process since a necessary number of cells are stored between the gates 166 and 167 for each incubator 186 (step 1426). More specifically, the controller 161 turns the gate 167 to the retreating state, and simultaneously supplies a predetermined number of cells to the incubator 186. Thereafter, the controller 161 resets v=0 (step 1428). Next, the controller 161 determines whether the total processing number A>the number of successfully injected cells k (step 1430). If A>k, supplies of all the cells to the incubator 186 have not yet completed and thus the controller 161 returns to the step 1406. On the other hand, when determining A is not greater than k, supplies of all the cells to the incubator 186 have completed. Therefore, the controller 161 sends the injection process termination signal to the host controller 141 (step 1432), and terminates the process.

On the other hand, when determining that the parameter C is not greater than the number of supplies i (step 1412), the injector 140 has processed a number of cells necessary to calculate the success rate and thus the controller 161 then determines whether the success rate's threshold O<the actual success rate x (step 1434). If O<x, the actual success rate is higher than the predetermined threshold and the controller 161 moves to the step 1414. On the other hand, if x is not higher than O, the actual success rate is not higher than the predetermined threshold and the controller 161 warns the host controller 141 or directly the operator of an adjustment (step 1440). As discussed above, the alarm may use voices through a speaker (not shown) or indications through a lamp (not shown). The controller 161 terminates the process after the step 1440.

On the other hand, when determining that the injection has failed (step 1418), the controller 161 increments j=j+1, u=u+1 (step 1436). Next, the controller 161 determines whether the threshold of the number of continuously unsuccessful injections N>the actual number of continuously unsuccessful injections u (step 1438). If N>u, the controller 161 moves to the step 1406 since the actual number of continuously unsuccessful injections is not higher than the predetermined threshold. On the other hand, if N is not greater than u, the actual number of continuously unsuccessful injections is higher than the predetermined threshold and the controller 161 warns the host controller 141 or directly the operator of an adjustment (step 1440).

Figure 13:
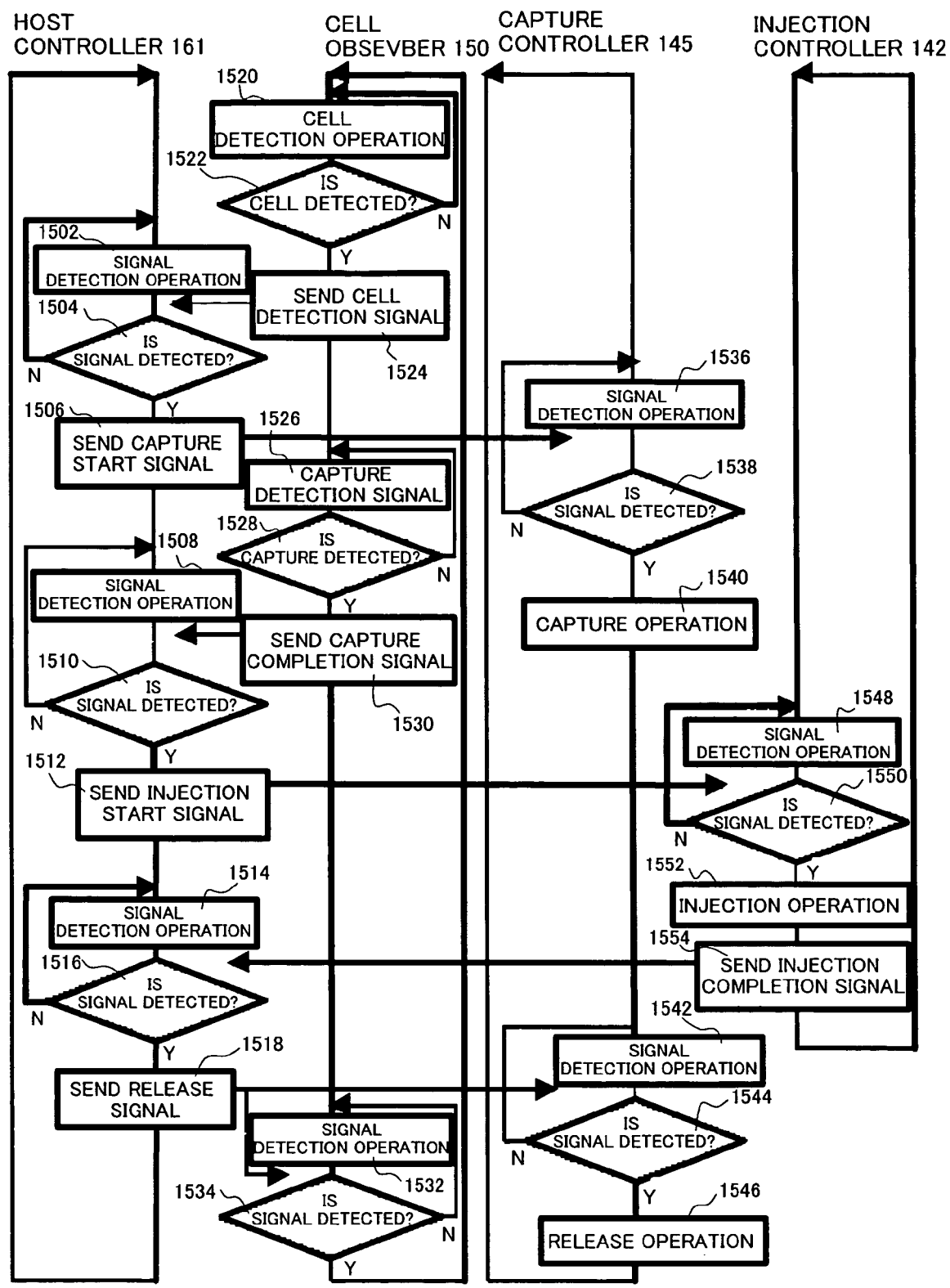
FIG. 13 is a timing chart for explaining operations of a host controller, an image processor, a capture controller, and an injection controller shown in FIG. 1.

FIG. 13 is a timing chart for explaining operations of the host controller 141, the cell observer 150, the capture controller 145 and the injection controller 142. The cell suspension 120 is filled in the feeder 118. If the cells are viscous cells, they have been peeled off from the carrier by a trypsin process. The mixer 124 mixes the filled cell suspension 120 with the medium 116 filled in the feeder 114, and dilutes the cells C to a proper concentration so as to inject the cells C individually. The cell suspension 120 that passes the mixer 124 is fed to the feed controlling apparatus 130 via the pipeline 102. The cell suspension 120 fed to the feed controlling apparatus 130 flows in the channel 158 in the injector 140 under the feed controlling process. The cell observer 150 observes the channels 131a and 158. In this state, the host controller 141, the capture controller 145, the injection controller 142 are moved to signal detecting states (steps 1502, 1536 and 1548).

The cell observer 150 monitors the channels 131a and 158 (step 1520). When detecting the cell C in the field of eye (step 1522), the cell observer 150 sends the cell detection information to the host controller 141 (step 1524), and again monitors the channels 131a and 158 (step 1526). In response (step 1504), the host controller 141 sends a capture start instruction to the capture controller 145 (step 1506), and waits for receiving the cell capture completion signal from the cell observer 150 (step 1508).

In response to the instruction from the host controller 141 (step 1538), the capture controller 145 controls the capture 146 member, and captures the cell C via the vacuum port 144 in the channel 158 as shown in FIG. 5 (step 1540). Thereafter, the capture controller 145 transfers to the signal detecting state (step 1542). The cell observer 150 sends the capture completion signal of the cell C to the host controller (step 1530) when detecting that the cell C stops in the field of eye (step 1528), and again transfers to the signal detecting state (step 1532).

In response (step 1510), the host controller 141 sends an injection start signal to the injection controller 142 (step 1512), and transfers to the signal detecting state (step 1514).

In response (step 1550), the injection controller 142 instructs the capillary 143 to start the injection. It is necessary in the instant embodiment, as described with reference to FIG. 6, that the injection controller 142 receives the ready signal directly from the controller 136 or via the host controller 141 (see step 1012 in FIG. 6). As a result, the capillary 143 pierces the cell membrane of the cell C captured by the capture member 146 via the fine hole 131g in FIG. 5, and injects a material, such as gene or medication, into the cell C (step 1552). The material may be filled in the capillary 143 or adhered to the tip of the capillary 143. When the material is filled in the capillary 143, the fluid supply unit in the injection controller 142 injects the proper amount. When the capillary 143 completes the injection operation, the injection controller 142 sends the injection termination signal to the host controller 141 (step 1554).

In response (step 1516), the host controller 141 sends a release signal to the cell observer 150 and the capture controller 145 (step 1518), and returns to the step 1502. In response (steps 1534 and 1544), the cell observer 150 terminates the signal detecting operation and returns to the step 1520, and the capture controller 145 controls the capture member 146 and releases the captured cell C (step 1546).

Part of the material injected cells is disposed to the collection container 169 via the feed controlling apparatus 160, and the rest is fed to the second feeding unit 170. The mixer 178 dilutes the cell C to a proper concentration using the medium 176 in the second feeding unit 170. The dispenser unit 180 dispenses the diluted cell suspension fed from the second feeding unit 170 via the nozzle 182 to the incubator 186 in the universal multi-hole plate 184. Thereby, each incubator 186 can store a predetermined concentration of cells so that respective cells can be handled individually. It is then possible to confirm the cloning of the cell and effect expressions of introduced gene and medication, if necessary.

As discussed above, according to the instant embodiment, the feed controlling apparatus 130 feeds the cells one by one to the injector 140 while maintaining the predetermined throughput. The feed controlling apparatus 160 feeds only the successfully injected cells by the injector 140 to the dispenser 180, enables the cells to be evaluated individually at a necessary concentration, and improves the precision in the subsequent analysis. The cell processing system uses the injection approach, thus maintains the high injection success rate without restricting a combination between a cell and an introduced material.

Thus, the present invention can provide a feed controlling apparatus and method, which improves the throughput and achieves an independent evaluation while adopting the injection approach that is free of a restriction of a combination of a cell and an introduced material, and has a high success rate.

What is claimed is:

1. A feed controlling apparatus comprising:
   a channel of a fluid configured to flow plural micro objects one by one in a single direction;
   a detector configured to detect a process to one of the plural micro objects at a predetermined position;
   a gate located upstream of the predetermined position and configured to open and close, the gate that opens allowing the object to be fed along the channel, and the gate that closes preventing the object from being fed along the channel; and
   a controller configured to control opening and closing of the gate based on a detection result by said detector.

2. A feed controlling apparatus comprising:
   a channel of a fluid configured to flow plural micro objects one by one in a single direction, the channel being branched into a first channel for a successfully processed object and a second channel for an unsuccessfully processed object;
   a detector configured to detect a process to one of the plural micro objects at a predetermined position;
   a first gate located downstream of the predetermined position and configured to open and close, the first gate that opens allowing the object to be fed to the first channel, and the first gate that closes preventing the object from being fed to the first channel; and
   a second gate located downstream of the predetermined position and configured to open and close, the second gate that opens allowing the object to be fed to the second channel, and the second gate that closes preventing the object from being fed to the second channel; and
   a controller configured to control opening and closing of the first and second gates based on a detection result by said detector.

3. A feed controlling apparatus according to claim 1, wherein said gate puts the objects on standby one by one in order along the channel.

4. A feed controlling apparatus according to claim 2, wherein said controller provides controls based on a size of the object.

5. A feed controlling apparatus according to claim 2, further comprising:
   a first counter configured to count the number of successes of the process by detecting that said first gate has opened; and
   a second counter configured to count the number of failures of the process by detecting that said second gate has opened,
   wherein said controller calculates at least one of a success rate of the process and a continuous failure number of the process based on detection results of said first and second counters, and warns of an operational abnormality based on a calculation result.

6. A feed controlling apparatus according to claim 2, wherein the channel for the successfully processed object is connected to a recovery part, and the predetermined process is an injection of a predetermined material into each cell in a cell suspension by using a capillary, wherein said feed controlling apparatus further comprises:
   a storage configured to store injected cells, and the controller simultaneously supplies a predetermined amount of injected cells to the recovery part when determining that the predetermined amount of injected cells are stored in said storage.

* * * * *